(12) United States Patent
Kurosaki et al.

(10) Patent No.: US 11,660,429 B2
(45) Date of Patent: *May 30, 2023

(54) DRUG COATING LAYER AND METHOD FOR FORMING SAME

(71) Applicant: TERUMO KABUSHIKI KAISHA, Tokyo (JP)

(72) Inventors: Yasuo Kurosaki, Kanagawa (JP); Yu Osawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 523 days.

This patent is subject to a terminal disclaimer.

(21) Appl. No.: 16/800,204

(22) Filed: Feb. 25, 2020

(65) Prior Publication Data

US 2020/0188643 A1 Jun. 18, 2020

Related U.S. Application Data

(63) Continuation of application No. PCT/JP2018/035040, filed on Sep. 21, 2018.

(30) Foreign Application Priority Data

Sep. 21, 2017 (JP) .............................. JP2017-181787

(51) Int. Cl.
| | |
|---|---|
| *A61M 25/10* | (2013.01) |
| *A61L 29/08* | (2006.01) |
| *A61L 29/14* | (2006.01) |
| *A61L 29/16* | (2006.01) |
| *A61K 9/16* | (2006.01) |
| *A61K 31/337* | (2006.01) |
| *A61K 31/436* | (2006.01) |
| *A61K 31/4418* | (2006.01) |

(52) U.S. Cl.
CPC ............ *A61M 25/104* (2013.01); *A61K 9/16* (2013.01); *A61K 31/337* (2013.01); *A61K 31/436* (2013.01); *A61K 31/4418* (2013.01); *A61M 2025/105* (2013.01); *A61M 2025/1075* (2013.01); *A61M 2025/1088* (2013.01)

(58) Field of Classification Search
None
See application file for complete search history.

(56) References Cited

U.S. PATENT DOCUMENTS

| | | |
|---|---|---|
| 2007/0134288 A1 | 6/2007 | Parsonage et al. |
| 2011/0143014 A1 | 6/2011 | Stankus et al. |
| 2012/0231037 A1 * | 9/2012 | Levi .................. A61L 31/16 |
| | | 118/69 |
| 2014/0271775 A1 * | 9/2014 | Cleek .................. A61L 27/54 |
| | | 427/2.25 |
| 2014/0358122 A1 * | 12/2014 | Yamashita .......... A61M 25/104 |
| | | 424/490 |
| 2015/0182732 A1 | 7/2015 | Zeng et al. |
| 2017/0014601 A1 | 1/2017 | Kurosaki et al. |

FOREIGN PATENT DOCUMENTS

| | | |
|---|---|---|
| CN | 104874090 A | 9/2015 |
| CN | 106075703 A | 11/2016 |
| CN | 106163602 A | 11/2016 |
| EP | 2 813 250 A1 | 12/2014 |
| EP | 3 106 197 A1 | 12/2016 |
| JP | 2014131748 A | 7/2014 |
| JP | 2015521530 A | 7/2015 |
| JP | 2016513543 A | 5/2016 |
| WO | 2010/086863 A2 | 8/2010 |
| WO | 2013146376 A1 | 10/2013 |
| WO | 2015151877 A1 | 10/2015 |

OTHER PUBLICATIONS

An English Translation of the International Search Report (Form PCT/ISA/210) and the Written Opinion of the International Searching Authority (Form PCT/ISA/237) dated Dec. 11, 2018, by the Japanese Patent Office in corresponding International Application No. PCT/JP2018/035040. (7 pages).

The extended European Search Report dated Jun. 25, 2020, by the European Patent Office in corresponding European Patent Application No. 18857490.9-1109. (9 pages).

(Continued)

*Primary Examiner* — Bethany P Barham
*Assistant Examiner* — Peter Anthopolos
(74) *Attorney, Agent, or Firm* — Buchanan Ingersoll & Rooney PC

(57) ABSTRACT

A drug coating layer that prevents breakage of elongated drug crystals on a balloon surface while maintaining the drug crystals in an appropriate shape to act on the living body includes plural elongated bodies which are crystals of a water-insoluble drug each extending from the surface of the balloon at various lengths and angles, and a water-soluble additive layer provided in a space between an outer surface of an aggregate of the elongated bodies and the balloon surface to fill a space between the elongated bodies. The outer surface of the additive layer being located outside the aggregate, being uneven connecting a plurality of tip ends and side surfaces of the elongated bodies to each other. The tip ends of the elongated bodies slightly protrude from the additive layer, and the side surfaces and/or tip surfaces of the elongated body are exposed on the surface of the additive layer.

20 Claims, 10 Drawing Sheets

(56) References Cited

OTHER PUBLICATIONS

Gao et al., "Efficacy of Rapamycin Drug-Eluting Stent in Coronary Interventional Therapy," Tianjin Medical Journal, (Feb. 28, 2007), vol. 35, No. 2, pp. 135-136, with partial machine-generated translation.
Office Action (The First Office Action) dated Jul. 21, 2021, by the State Intellectual Property Office of People's Republic of China in corresponding Chinese Patent Application No. 201880052034.1 and an English Translation of the Office Action. (13 pages).
International Search Report (PCT/ISA/210) dated Dec. 11, 2018, by the Japanese Patent Office as the International Searching Authority for International Application No. PCT/JP2018/035040.
Written Opinion (PCT/ISA/237) dated Dec. 11, 2018, by the Japanese Patent Office as the International Searching Authority for International Application No. PCT/JP2018/035040.

\* cited by examiner

DRUG COATING LAYER AND METHOD FOR FORMING SAME

CROSS-REFERENCES TO RELATED APPLICATIONS

This application is a U.S. national-stage entry of International Patent Application No. PCT/JP2018/035040 filed on Sep. 21, 2018, and claims priority to Japanese Application No. 2017-181787 filed on Sep. 21, 2017, the entire content of both of which is incorporated herein by reference.

FIELD OF THE INVENTION

The present invention relates generally to a drug coating layer provided on a surface of a balloon and a method for forming the same.

BACKGROUND DISCUSSION

In recent years, a balloon catheter has been used in order to improve lesion areas (stenosed sites) generated in a body lumen. Generally, the balloon catheter includes an elongated shaft portion and a balloon capable of inflating in a radial direction and provided on a distal side of the shaft portion. After the balloon in a deflated state reaches a target area in a body via a small body lumen, the balloon is inflated and the lesion area is thus widened.

However, when the lesion area is forcibly widened, excessive proliferation of smooth muscle cells may occur to induce new stenosis (restenosis) in the lesion area. For this reason, recently, a drug eluting balloon (DEB) in which a surface of the balloon is coated with a drug for preventing stenosis has been used. The drug elution balloon can instantaneously release the drug coated on the surface of the balloon by being inflated to the lesion area, thereby preventing restenosis.

In recent years, it has been becoming apparent that a morphological form of the drug coated on the surface of the balloon affects a releasing property of the drug from the balloon surface or tissue transferability in the lesion area. An example of a balloon catheter in which drug crystals with an elongated shape are formed on the surface of the balloon is disclosed in U.S. Patent Application Publication No. 2014/0271775.

An example of a balloon catheter in which an adhesive layer, a first layer containing a treatment agent and an additive, and a second layer containing an additive are provided on a surface of a balloon is disclosed in Japanese Patent Application Publication No. 2014-131748.

SUMMARY

The elongated crystals formed on the surface of the balloon may be broken due to the long and thin shape. For example, since a force is applied to the surface of the balloon when the balloon is folded, the elongated crystals are likely to be broken. When the crystals are broken, the broken crystals are fallen off from the balloon at the time of transporting the balloon in a blood vessel, resulting in an undesirable effect on a living body.

A drug coating layer is disclosed, which is capable of preventing breakage of elongated drug crystals on a surface of a balloon and maintaining the drug crystals in an appropriate shape in order to act on the living body, and a method for forming the same.

A drug coating layer is disclosed which is formed on a surface of a balloon, and the drug coating layer includes: a plurality of elongated bodies which are crystals of a water-insoluble drug and each have a long axis extending from the surface of the balloon at various lengths and angles; and a water-soluble additive layer which is provided in a space between an outer surface of a cluster (an aggregate) of the plurality of elongated bodies and the surface of the balloon so as to fill a space between the elongated bodies, the outer surface being located outside the cluster and having an unevenness connecting a plurality of tip ends and side surfaces of the elongated bodies to each other, in which the tip ends of the elongated body slightly protrude from the additive layer, and the side surfaces and/or tip surfaces of the elongated body are exposed on a surface of the additive layer.

A method for forming a drug coating layer is disclosed in which a plurality of elongated bodies which are crystals of a water-insoluble drug and each have a long axis are formed on a surface of a balloon, and the method includes: supplying a first coating solution which contains a water-insoluble drug, a first water-soluble additive, an organic solvent, and water to the surface of the balloon and evaporating the organic solvent and the water to form a first additive layer containing the first water-soluble additive and the elongated bodies protruding from the first additive layer; and supplying a second coating solution which contains a second water-soluble additive and water to the first additive layer and the elongated bodies and evaporating the water to form a second additive layer so as to fill a space between the elongated bodies protruding from the first additive layer.

In the drug coating layer configured as described above, since the tip end of the elongated body, which is a drug crystal having a long axis slightly protrudes from the additive layer, the elongated body on the surface of the balloon can be prevented from being broken by the additive layer and maintain the elongated body in an appropriate shape in order to act on the living body. Furthermore, since the side surface and/or the tip surface of the elongated body is exposed to the surface of the additive layer, the additive layer does not interfere with transferability in blood vessel of the elongated body, which is a drug, without excessively embedding the elongated body in the additive layer.

The additive layer may have a first additive layer provided on the surface of the balloon, and a second additive layer provided to cover the outside of the first additive layer and fill a space between elongated bodies protruding from the first additive layer. Thus, the breakage of the elongated body can be prevented by the second additive layer while properly holding the elongated body on the surface of the balloon by the first additive layer.

The first additive layer and the second additive layer contain the same or different water-soluble low molecular weight compounds. Thus, the first additive layer and the second additive layer are rapidly dissolved in the blood vessel, and thus do not interfere with the transferability in blood vessel of the elongated body which is a drug. In a case where the first additive layer and the second additive layer contain the different water-soluble low molecular compounds, the additive which is likely to form the elongated body on the surface of the balloon can be used for the first additive layer and the additive which is likely to prevent the breakage of the elongated body can be used for the second additive layer. In a case where the first additive layer and the second additive layer contain the same water-soluble low molecular weight compound, the same additive may be used for the second additive layer after the additive which is likely to form the elongated body on the surface of the balloon is used for the first additive layer, or the second additive layer may be formed simultaneously when the first additive layer is formed.

The water-insoluble drug may contain at least one selected from the group consisting of rapamycin, paclitaxel, docetaxel, and everolimus. Thus, it is possible to properly prevent restenosis of the stenosed site in the blood vessel due to the elongated body which is a drug crystal.

In the method for forming a drug coating layer configured as such, it is possible to securely form the first additive layer and the elongated body, which is a drug crystal, having a long axis and protruding from the first additive layer, using the appropriate amount of the first water-soluble additive. Thereafter, the second additive layer is formed to fill the space between the elongated bodies, thereby preventing the breakage of the elongated body which is a drug and maintaining the elongated body in an appropriate shape in order to act on the living body.

BRIEF DESCRIPTION OF THE DRAWINGS

FIG. 10A illustrates a state before the balloon is folded, FIG. 10B illustrates a state in which the pleat portions are formed by the pleating section, and FIG. 10C illustrates a state in which the pleat portions are folded by the folding section.

FIG. 11A illustrates a state in which a first additive layer is formed on a surface of a balloon, and FIG. 11B illustrates a state in which a second additive layer is formed.

FIG. 12A illustrates an example of the drug coating layer according to the second embodiment, and FIG. 12B illustrates another example of the drug coating layer according to the first embodiment.

DETAILED DESCRIPTION

Set forth below with reference to the accompanying drawings is a detailed description of embodiments of a drug coating layer provided on a surface of a balloon and a method for forming the same, representing examples of the inventive drug coating layer and method disclosed here. The dimensions or scales on the drawings may be exaggerated or different from actuality/reality for convenience of description and illustration.

Figure 1:
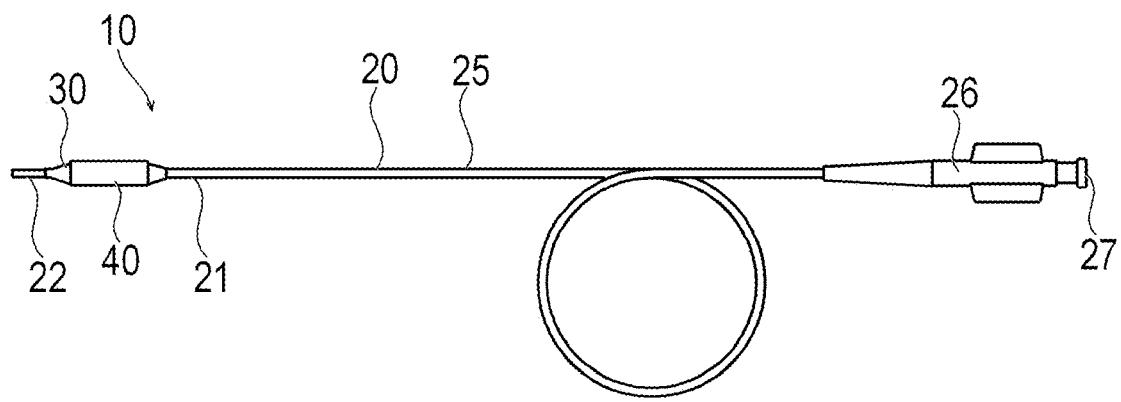
FIG. 1 is a front view illustrating a balloon catheter having a drug coating layer according to a first embodiment.
Figure 2:
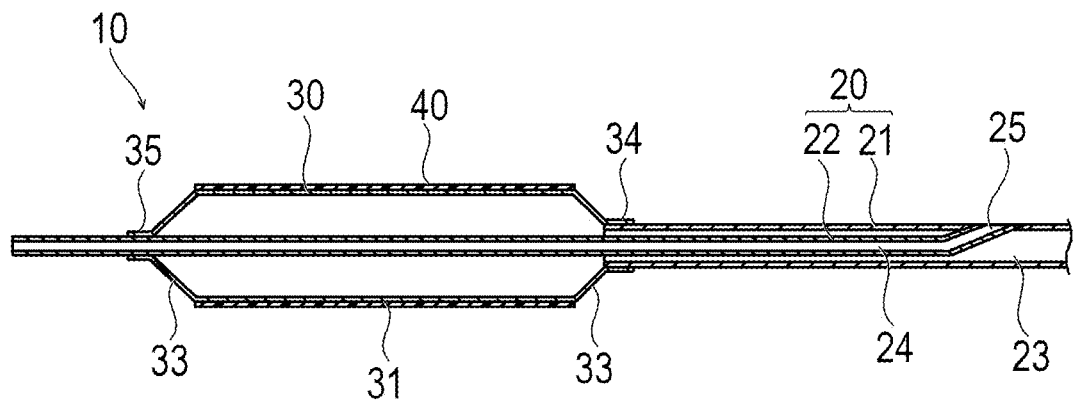
FIG. 2 is a cross-sectional view of a distal portion of the balloon catheter.
Figure 3:
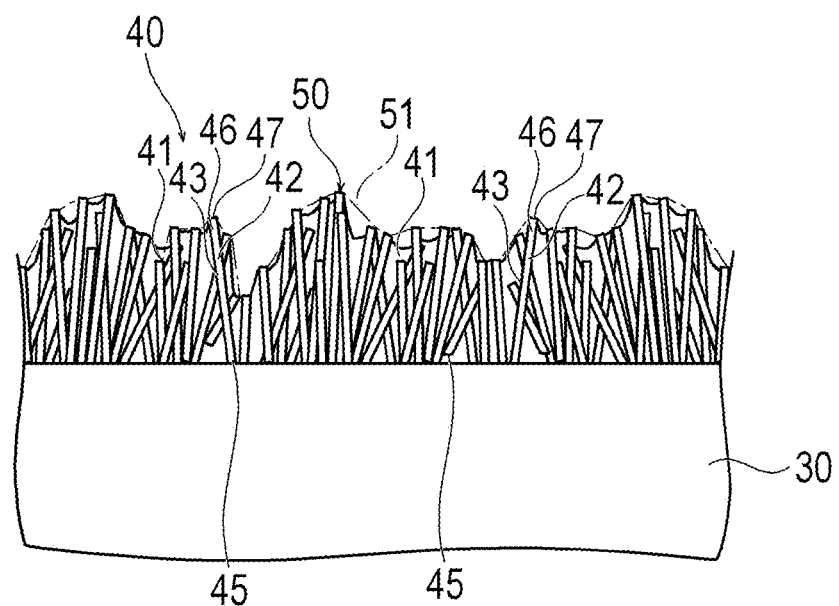
FIG. 3 is a cross-sectional view illustrating the drug coating layer on a surface of the balloon.

According to a first embodiment of the drug coating layer provided on a surface of a balloon disclosed herein, a drug coating layer 40 is provided on a surface of a balloon 30 of a drug eluting type balloon catheter 10 as illustrated in FIGS. 1 to 3. In the present disclosure, a side of the balloon catheter 10 to be inserted into a body lumen refers to a "distal side" and an operating hand-side refers to a "proximal side".

A configuration of the balloon catheter 10 is described herein. The balloon catheter 10 includes an elongated catheter main body 20, the balloon 30 provided on a distal portion of the catheter main body 20, the drug coating layer 40 provided on the surface of the balloon 30, and a hub 26 fixed to a proximal end of the catheter main body 20.

The catheter main body 20 includes an outer tube 21 which is a tube body in which the distal end and the proximal end are open and an inner tube 22 which is a tube body disposed or positioned inside or inserted into the outer tube 21. The inner tube 22 is housed inside a hollow of the outer tube 21, and a distal portion of the catheter main body 20 has a double tube structure. In the hollow of the inner tube 22, a guide wire lumen 24 for inserting guide wire is provided. In addition, an inflation lumen 23 for circulating inflation fluid in the balloon 30 is formed inside the hollow of the outer tube 21, that is, outside the inner tube 22. The inner tube 22 is opened to the outside of an opening portion 25. The inner tube 22 protrudes further toward a distal side than the distal end of the outer tube 21. A distal tip as a separate member may be provided at the distal portion of the inner tube 22.

In the balloon 30, a balloon fusing section (balloon fixing section) 34 at a proximal end portion is fused (fixed) at the distal portion of the outer tube 21 and a balloon fusing section (balloon fixing section) 35 at a distal end portion is fused (fixed) at the distal portion of the inner tube 22. A method for fixing the balloon 30 to the outer tube 21 and the inner tube 22 is not limited to the fusing, and for example, may be adhered. Thus, the inside of the balloon 30 communicates with the inflation lumen 23. The inflation fluid is injected to the balloon 30 through the inflation lumen 23, such that the balloon 30 can be inflated. The inflation fluid may be gas or liquid. For example and without limitation, one or more gases such as helium gas, $CO_2$ gas, $O_2$ gas, $N_2$ gas, Ar gas, air, and mixed gas may be used. In another aspect and without limitation, one or more liquids such as a physiological salt solution and a contrast agent can be used as the inflation fluid.

At a central portion of the balloon 30 in an axial direction, a cylindrical straight section 31 (inflatable portion) having an outer diameter equal to an outer diameter of the balloon is formed at the time of inflating the balloon and a tapered portion 33 having an outer diameter being gradually changed is formed at both sides of the straight section 31 in the axial direction. Then, the drug coating layer 40 containing a drug is formed on the entire surface of the straight section 31. In the balloon 30, a range in which the drug coating layer 40 is formed is not limited only to the straight section 31, and may include at least a part of the tapered portion 33 in addition to the straight section 31 or only a part of the straight section 31.

A proximal opening portion 27, which serves as a port communicating with the inflation lumen 23 of the outer tube 21 and to allow the inflation fluid to flow in and out, is formed at the hub 26.

A length of the balloon 30 in the axial direction is not particularly limited, and may preferably be 5 to 500 mm, more preferably 10 to 300 mm, and still more preferably 20 to 200 mm. An outer diameter of the balloon 30 at the time of inflating is not particularly limited, and may preferably be 1 to 10 mm and more preferably 2 to 8 mm.

A surface of the balloon 30 before the drug coating layer 40 is formed or applied is smooth and nonporous. The surface of the balloon 30 before the drug coating layer 40 is formed may have recesses or blind holes which do not penetrate a film forming the balloon. In addition, the surface of the balloon 30 before the drug coating layer 40 is formed or applied may be both a smooth, nonporous surface and a surface having blind holes or recesses which do not penetrate the film. That is, some parts of the surface of the balloon 30 before the drug coating layer 40 is applied may be a smooth, nonporous surface and other parts of the surface of the balloon 30 before the drug coating layer 40 is applied may have blind holes or recesses. The blind holes (recesses) may have, for example, a diameter of from 0.1 to 5 μm and a depth of from 0.1 to 10 μm. As described in more detail below, the drug coating layer preferably includes upstanding elongated crystals of a water-insoluble drug. The diameter and depth of the blind holes noted above are selected so that the blind holes individually receive one of the elongated crystals (e.g., the proximal end of one elongated crystal is positioned in one blind hole, the proximal end of another elongated crystal is received in a different blind hole, etc.) or so that each of a plurality of the blind holes receives a portion of one of the elongated crystals (e.g., one portion of the proximal end of an elongated crystal is received in one blind hole, another portion of the proximal end of the same elongated crystal is positioned in a different blind hole, etc.). In addition, the one or more blind holes may have, for example, a diameter of from 5 to 500 μm and a depth of from 0.1 to 50 μm. These size ranges for the diameter and depth may apply for blind holes that receive one elongated crystal (i.e., the proximal end of one elongated crystal is positioned in each blind hole or the proximal ends of more than one elongated crystal is positioned in each blind hole). Each of the blind holes that contains an elongated crystal, part of an elongated crystal or plural elongated crystals are configured so that the elongated crystals project out from the blind hole.

It is preferable that the balloon 30 has both some flexibility, and simultaneously, some rigidity so as to be inflated when the balloon 30 reaches the blood vessel, a tissue, or the like and release the drug contained in the surface of the balloon from the drug coating layer 40. Specifically, the balloon 30 is formed of a metal or a resin, but at least the surface of the balloon 30 on which the drug coating layer 40 is provided is preferably formed of a resin. Examples of constituent materials of at least the surface of the balloon 30 include polyolefins such as polyethylene, polypropylene, polybutene, an ethylene-propylene copolymer, an ethylene-vinyl acetate copolymer, ionomer, or a mixture of two or more kinds thereof, and thermoplastic resins such as a soft polyvinyl chloride resin, polyamide, polyamide elastomer, nylon elastomer, polyester, polyester elastomer, polyurethane, and a fluororesin, silicone rubber, latex rubber, and the like. Among these, polyamides are preferable. That is, at least a part of the surface of the balloon 30 coated with the drug is polyamides. The polyamides are not particularly limited as long as it is a polymer having an amide bond and examples thereof include aromatic polyamides, for example, homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), and polydodecanolactam (nylon 12), copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), and caprolactam/hexamethylenediammonium adipate copolymer (nylon 6/66), copolymer of adipic acid with metaxylenediamine, and copolymers of hexamethylenediamine with m,p-phthalic acids, and the like. Furthermore, polyamide elastomers which are block copolymers having nylon 6, nylon 66, nylon 11, nylon 12, or the like as a hard segment and having a polyalkylene glycol, a polyether, an aliphatic polyester, or the like as a soft segment can also be used as a material for the balloon 30. The polyamides may be used alone or in combination of two or more kinds thereof. In certain embodiments, the balloon 30 has a smooth surface formed of polyamide.

The drug coating layer 40 is formed or applied on the surface of the balloon 30 directly or through a pre-processing layer such as a primer layer by a method described below. As illustrated in FIG. 3, the drug coating layer 40 includes an additive layer 41 (diluting agent layer) containing a water-soluble low molecular weight compound and disposed on the surface of the balloon 30 in a form of a layer, and a plurality of upstanding elongated bodies 42 which are crystals of the water-insoluble drug and each have an independent long axis (longitudinal axis or central axis). A proximal end 45 of at least some of the elongated bodies 42 directly contact the surface of the balloon 30. Elongate bodies 42 in which the proximal end 45 does not come into contact with the surface of the balloon 30 may also exist. The tip end 46 of the elongated bodies 42 slightly protrudes from the additive layer 41. That is, the tip end 46 of at least some of the elongated bodies 42 slightly protrudes from the additive layer 41 so that such tip ends are exposed outside the additive layer 41. Therefore, a length of a part of the elongated body 42 protruding from a surface of the additive layer 41 toward the outside is shorter than a length of a part of the elongated body 42 located in the additive layer 41. In other words, the length of the portion of the elongated bodies 42 that is exposed outside the additive layer 41 is less than the length of the portion of the elongated bodies 42 embedded in the additive layer 41. The surface of the drug coating layer 40 does not have a constant height from the surface of the balloon 30. Rather, the outer surface of the drug coating layer 40 has an undulating shape in some extent. Therefore, the surface of the drug coating layer 40 has an unevenness (i.e., the outer surface of the drug coating layer undulates or has an undulating configuration). The unevenness (undulations) may be regular. The outer surface of the drug coating layer 40 is formed by the surface of the additive layer 41, the exposed side surfaces 43 and the exposed tip surfaces 47 of the elongated bodies 42 located on a surface layer of the additive layer 41. That is, at least a portion of the side surface 43 and the tip surface 47 of at least some of the elongated bodies 42 may be exposed from the surface of the additive layer 41 (i.e., the tip surface of some of the elongated bodies may be exposed (i.e., not covered by the additive layer) and a part of the side surface of such elongated bodies may be exposed (i.e., not covered by the additive layer)).

In certain embodiments, a plurality of elongated bodies 42 may be regularly arranged on the surface of the balloon 30. In other embodiments, the plurality of elongated bodies 42 may be irregularly arranged on the surface of the balloon 30.

An inclination angle of the long axis of the elongated body 42 to the surface of the balloon 30 is not particularly limited, and the inclination angle thereof may be from 45 degrees to 135 degrees, preferably 60 degrees to 120 degrees, more preferably 75 degrees to 105 degrees, and still more preferably about 90 degrees.

An amount of drug contained in the drug coating layer 40 is not particularly limited, and the drug may be contained at a concentration of 0.1 $\mu g/mm^2$ to 10 $\mu g/mm^2$, preferably 0.5 $\mu g/mm^2$ to 5 $\mu g/mm^2$, more preferably 0.5 $\mu g/mm^2$ to 3.5 $\mu g/mm^2$, still more preferably 1.0 $\mu g/mm^2$ to 3 $\mu g/mm^2$. An amount of crystals of the drug coating layer 40 is not particularly limited, and may preferably be 5 to 500,000 crystals/10 $\mu m^2$ (i.e., the number of crystals per 10 $\mu m^2$), more preferably 50 to 50,000 crystals/10 $\mu m^2$, and still more preferably 500 to 5,000 crystals/10 $\mu m^2$.

The plurality of the elongated bodies 42 each having an independent long axis may exist in a state in which the elongated bodies 42 are combined (i.e., when the elongated bodies contact one another). The plurality of adjacent elongated bodies 42 may contact each other in a state in which the adjacent elongated bodies have different angles from each other. That is, some of the adjacent elongated bodies may contact one another by virtue of the elongated bodies being angled at different angles relative to a common orientation. The plurality of elongated bodies 42 may be positioned on the surface of the balloon such that some adjacent elongated bodies 42 are spaced apart from one another so that a space exists between adjacent elongated bodies. In either case in which the plurality of elongated bodies 42 are in a combined state or where the plurality of elongated bodies 42 are spaced apart from each other, the elongated bodies 42 may exist on the surface of the balloon 30. The plurality of elongated bodies 42 may have different long axis directions and may be arranged in a circular shape as a brush shape. Each of the elongated bodies 42 exists independently, has a certain length, and has one end (proximal end 45) that is fixed to the additive layer 41 or to the balloon 30. The elongated body 42 is not interlocked with the adjacent elongated body 42 without forming a complex structure (i.e., elongated bodies are independent of one another and not fixed to each other). In an aspect, the long axis of the elongated body 42 is substantially linear.

It is preferable that the elongated bodies 42 each stand alone without being in contact with each other. The proximal end 45 of elongated bodies 42 may be in contact with the proximal end 45 of other elongated bodies on the balloon 30. In addition, the proximal end 45 of the elongated body 42 may stand alone without being in contact with the other proximal end 45 on the balloon 30.

The elongated bodies 42 may be hollow or solid. Hollow elongated bodies 42 and solid elongated bodies 42 may both exist on the surface of the balloon 30. In a case where the elongated body 42 is hollow, at least the tip end of the elongate body 42 is hollow. A cross section of the elongated body 42 in a plane perpendicular to the long axis of the elongated body 42 is hollow. The cross section of the elongated body 42 having the hollow in a plane perpendicular to the long axis of the elongated body 42 is polygonal. The polygon may be, for example, a triangle, a tetragon, a pentagon, a hexagon, or the like. Therefore, the elongated body 42 having the tip end 46 (or the tip surface 47) and the proximal end 45 (or the proximal surface) has the side surface(s) between the tip end 46 (or the tip surface 47) and the proximal end 45 (or the proximal surface) that is formed as an elongated polyhedron constituted of a plurality of substantial planes. In addition, the elongated body 42 may have a needle shape. In this crystal morphological form (crystal morphological form of a hollow elongated body), the bottom surface of the proximal end 45 is configured to be either entirely or at least part of a plane on the surface.

A length of the elongated bodies 42 having a long axis in the long axial direction may preferably be 5 µm to 20 µm, more preferably 9 µm to 11 µm, and still more preferably about 10 µm. A diameter of the elongated bodies 42 having a long axis may preferably be 0.01 µm to 5 µm, more preferably 0.05 µm to 4 µm, and still more preferably 0.1 µm to 3 µm.

In certain embodiments, the elongated bodies 42 having the long axis (elongated shape) described above constitute an amount equal to or more than 50% by volume with respect to the total amount of drug crystals on the surface of the balloon 30, and more preferably equal to or more than 70% by volume with respect to the total amount of drug crystals contained in the surface of the balloon 30. A remainder of the drug crystals are other than elongated bodies. That is, the drug coating layer 40 may be comprised of the additive layer 41, drug crystals in the form of the elongated bodies 42, and drug crystals in a form other than elongated bodies.

A cluster 50 of elongated bodies is formed of a plurality of the elongated bodies 42. There may be multiple clusters of elongated bodies. The elongated bodies 42 in a cluster 50 may include elongated bodies in contact with the balloon outer surface, elongated bodies spaced from the outer surface of the balloon 30 at different distances and elongated bodies oriented at different angles. The drug coating layer has an outer surface 50 located outside the cluster 51 and connecting a plurality of tip ends 46 and side surfaces 43.

The outer surface 51 of the drug coating layer has an unevenness (i.e., the outer surface of the drug coating layer undulates or has an undulating configuration). The additive layer 41 is provided in a space between the outer surface of the balloon 30 and the outer surface 50 (i.e., the outer surface of the additive layer and the tips of the elongate bodies (clusters)). The tip ends 46 of the elongated bodies 42 slightly protrude from the additive layer 41. That is, the tip ends 46 of at least some of the elongated bodies 42 slightly protrude from the additive layer 41 so that such tip ends are exposed outside the additive layer 41. The side surface 43 and/or tip surface 47 of the elongated bodies 42 located on the outer surface 51 of the elongated bodies cluster is exposed from the surface of the additive layer 41. There are also elongated bodies 42 embedded in the additive layer 41 which have no exposed portion. The additive layer 41 exists to be distributed into spaces between the plurality of elongated bodies 42 standing or positioned close together. The additive layer 41 may exist in a region where there are the elongated bodies 42 and may not exist in a region where there are no elongated bodies 42. An additive constituting the additive layer 41 may not form a matrix. The additive constituting the additive layer 41 may form a matrix. The matrix is a layer in which relative polymer substances (polymers, or the like) are continuously constituted, forms a mesh-shaped three-dimensional structure, and a fine space exists in the matrix. Therefore, the water-insoluble drug constituting crystals is not adhered to the matrix substances. The water-insoluble drug constituting crystals is not embedded in the matrix substances.

The additive layer 41 is formed as a layer by coating the additive layer on the surface of the balloon 30 in a water-soluble state and then drying the additive layer. The additive layer 41 is an amorphous layer. The additive layer 41 may have crystal particles. In addition, the additive layer 41 may be formed as an independent layer that does not contain a water-insoluble drug. A thickness of the additive layer 41 is not particularly limited, and for example, may be preferably 0.5 to 20 μm. A length of a part of the elongated body 42 protruding from the surface of the additive layer 41 toward the outside is not particularly limited, and may be, for example, from 0 to 1 μm (i.e., so that the elongated body slightly protrudes outwardly from the surface of the additive layer 41).

At the time of delivering the drug to the body, the drug coating layer 40 including the elongated bodies 42 having the long axis exhibits low toxicity and a high stenosis inhibiting effect. In a case where the elongated bodies 42 has a hollow crystal structure, since a unit of crystals becomes small when the drug is transferred to a tissue, the elongated bodies have good permeability to the tissue and good solubility. Therefore, the drug is efficiently acted to prevent stenosis. In addition, since the drug remaining in a tissue as a large mass is small, the toxicity is low.

In addition, the drug coating layer 40 has the plurality of substantially uniform elongated bodies 42 each having a long axis and substantially uniform morphological forms. The proximal ends of some of the elongated bodies 42 of crystals contact the outer surface of the balloon 30 and some of the elongated bodies of crystals are parallel to one another while extending away from (standing on) the surface of the balloon 30. Therefore, a size (a length in the long axis or longitudinal/axial direction) of crystals transferred to the tissue is as small as about 10 μm. Therefore, the drug is uniformly acted on a target lesion, such that the permeability in tissue is high. Furthermore, since a dimension of crystals to be transferred is small, an excessive amount of drug no longer remains in a target lesion for an excessive time. Therefore, the high stenosis inhibiting effect can be exhibited without exhibiting toxicity.

The drug coated on the surface of the balloon 30 may include an amorphous form. The crystals or amorphous forms may be arranged in the drug coating layer 40 so as to have regularity. In addition, the crystals or amorphous forms may be irregularly arranged.

Next, a balloon coating system for forming the above-described drug coating layer 40 on the balloon 30 will be described. This system includes a balloon coating apparatus 60 for forming the drug coating layer 40 on the balloon 30 (see FIG. 4) and a balloon folding apparatus for folding the balloon 30 on which the drug coating layer 40 is formed (see FIGS. 6 and 8).

Figure 4:
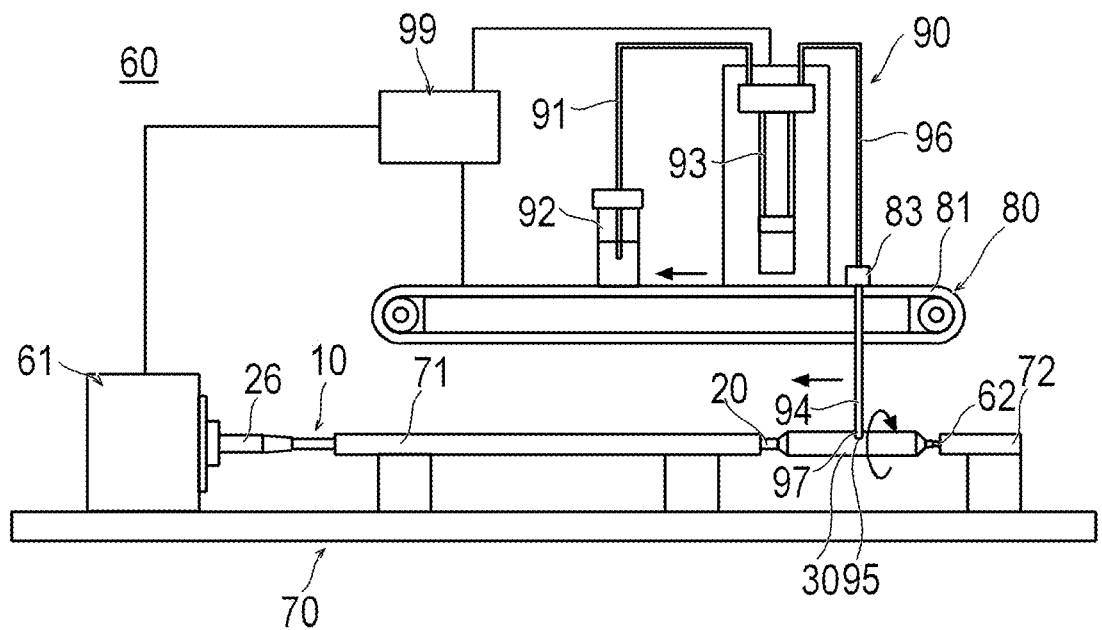
FIG. 4 is a front view illustrating a balloon coating apparatus.
Figure 5:
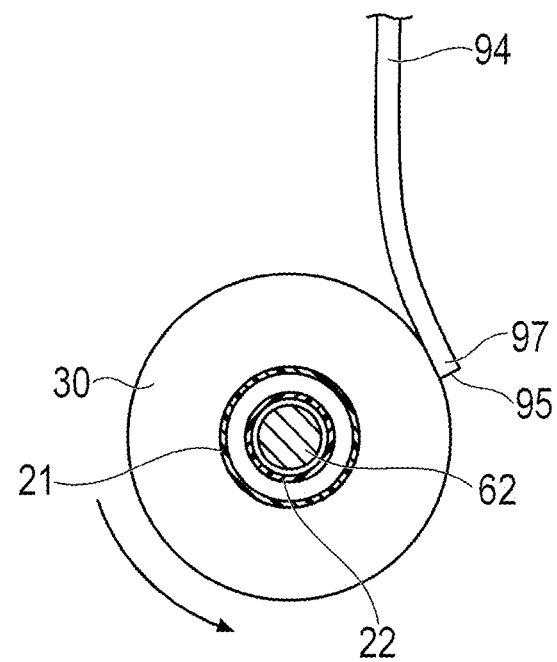
FIG. 5 is a cross-sectional view illustrating a dispensing tube in contact with the balloon.

First, the balloon coating apparatus 60 will be described. As illustrated in FIGS. 4 and 5, the balloon coating apparatus 60 includes a rotating mechanism section 61 rotating the balloon catheter 10 and a supporting table 70 for supporting the balloon catheter 10. The balloon coating apparatus 60 further includes an applying mechanism section 90 provided with a dispensing tube 94 that applies a coating solution to the surface of the balloon 30, a moving mechanism section 80 for moving the dispensing tube 94 relative to the balloon 30, and a control unit 99 controlling the balloon coating apparatus 60.

The rotating mechanism section 61 holds the hub 26 of the balloon catheter 10 and rotates the balloon catheter 10 around an axis of the balloon 30 by a driving source such as a motor built therein. A core 62 in the guide wire lumen 24 is inserted through the balloon catheter 10 and held, and the flow of the coating solution in the guide wire lumen 24 is prevented by the core 62. In addition, since the balloon catheter 10 operates so that fluid is conveyed to the inflation lumen 23 to dilate or expand the lumen, a three-way stopcock capable of opening/closing a flow path is connected to the proximal opening portion 27 of the hub 26.

The supporting table 70 includes a pipe-shaped or tubular proximal support portion 71 accommodating the catheter main body 20 inside thereof and rotatably supporting the catheter main body and a distal support portion 72 for rotatably supporting the core 62. The distal support portion 72 may rotatably support a distal portion of the catheter main body 20 instead of the core 62, if possible.

The moving mechanism section 80 includes a moving table 81 capable of moving linearly in a direction parallel to the axis of the balloon 30 and a tube fixing section 83 to which is fixed the dispensing tube 94. The moving table 81 can move linearly by a driving source such as a motor built therein. The tube fixing section 83 fixes an upper end of the dispensing tube 94 to the moving table 81. Therefore, the moving table 81 is moved, thereby moving the dispensing tube 94 linearly in the direction parallel to the axis of the balloon 30. In addition, the applying mechanism section 90 is positioned on the moving table 81 and the applying mechanism section 90 is moved linearly in both directions along the axis.

The applying mechanism section 90 is a part that applies the coating solution to the surface of the balloon 30. The applying mechanism section 90 includes a container 92 storing the coating solution, a liquid delivering pump 93 feeding the coating solution at any feeding amount, and the dispensing tube 94 applying the coating solution to the balloon 30.

The liquid delivering pump 93 is a syringe pump for example, controlled by the control unit 99. The liquid delivery pump 93 sucks the coating solution from the container 92 through a suction tube 91, and thus can supply the coating solution to the dispensing tube 94 through a supply tube 96 at a desired feeding amount. The liquid delivering pump 93 is placed on the moving table 81 and can move linearly by the movement of the moving table 81. The liquid delivering pump 93 is not limited to a syringe pump as long as the liquid delivering pump can feed the coating solution, and may be, for example, a tube pump.

The dispensing tube 94 is a member for communicating with the supply tube 96 and ejecting the coating solution supplied from the liquid delivering pump 93 through the supply tube 96 to the surface of the balloon 30. The dispensing tube 94 is a cylindrical member having flexibility. The dispensing tube 94 has an opening portion 95 fixed to the upper end of the tube fixing section 83, extending vertically downward from the tube fixing section 83, and formed in an ejecting end 97 which is a lower end. The dispensing tube 94 moves the moving table 81, such that it is possible to move linearly in both directions along the axial direction of the balloon catheter 10 together with the liquid delivering pump 93 placed on the moving table 81. The dispensing tube 94 can supply the coating solution to the surface of the balloon 30 in a state where the dispensing tube is pressed against the balloon 30 and bent.

The dispensing tube 94 may be a cylindrical shape as long as the coating solution is supplied. In addition, the dispensing tube 94 may not extend in the vertical direction as long as the coating solution is ejected from the opening portion 95.

It is preferable that the dispensing tube 94 is formed of a flexible material so that a contact load in contact with the balloon 30 can be reduced and change in a contact position in accordance with the rotation of the balloon 30 can be absorbed by bending. Examples of a constituent material of the dispensing tube 94 include, but are not limited to, polyolefins such as polyethylene, polypropylene, and the like, cyclic polyolefins, polyesters, polyamides, polyurethanes, and fluororesins such as polytetrafluoroethylene (PTFE), tetrafluoroethylene-ethylene copolymer (ETFE), tetrafluoroethylene-perfluoroalkylvinyl ether copolymer (PFA), tetrafluoroethylene-hexafluoropropylene copolymer (FEP), and the like. The constituent material is not limited as long as the constituent material is flexible and deformable.

An outer diameter of the dispensing tube 94 is not limited and, for example, may preferably be 0.1 mm to 5.0 mm. An inner diameter of the dispensing tube 94 is not particularly limited and, for example, may be from 0.05 mm to 3.0 mm. A length of the dispensing tube 94 is not limited, and may be a length five times or less the diameter of the balloon. For example, the length of the dispensing tube may be from 1.0 mm to 50 mm.

The control unit 99 is composed of, for example, a computer, and generally controls the rotating mechanism section 61, the moving mechanism section 80, and the applying mechanism section 90. The, control unit 99 can generally control a rotational speed of the balloon 30, a moving speed of the dispensing tube 94 to the axial direction with respect to the balloon 30, and an ejecting rate of the drug from the dispensing tube 94, and other parameters.

The coating solution supplied to the balloon 30 by the dispensing tube 94 is a solution or a suspension containing the constituent material of the drug coating layer 40 and contains a water-insoluble drug, an additive (diluting agent), an organic solvent, and water. After the coating solution is supplied to the surface of the balloon 30, an organic solvent and water are volatilized, and thus the drug coating layer 40 having the plurality of elongated bodies 42 which are crystals of the water-insoluble drug and each have an independent long axis is formed on the surface of the balloon 30.

Viscosity of the coating solution may be from 0.5 to 1500 cP, preferably 1.0 to 500 cP, and more preferably 1.5 to 100 cP.

The water-insoluble drug means a drug which is insoluble or hardly soluble in water. In an aspect, the solubility of the water-insoluble drug in water is less than 1 mg/mL at pH 5 to 8. In certain embodiments, the solubility of the water-insoluble drug may be less than 0.1 mg/mL. In certain embodiments, the water-insoluble drug is one or more fat-soluble drugs.

Some preferred examples of the water-insoluble drug include immunosuppressive drugs such as cyclosporines including cyclosporine, immunoactive drugs such as rapamycin, anticancer drugs such as paclitaxel, antiviral drugs or antibacterial drugs, antineoplastic tissue drugs, analgesic drugs, anti-inflammatory drugs, antibiotic drugs, antiepileptic drugs, anxiolytic drugs, antiparalysis drugs, antagonists, neuron blocking drugs, anticholinergic drugs, cholinergic drugs, antimuscarinic drugs, muscarinic drugs, antiadrenergic drugs, antiarrhythmic drugs, antihypertensive drugs, hormone drugs, and nutritional supplements.

In certain embodiments, the water-insoluble drug may be preferably at least one selected from the group consisting of rapamycin, paclitaxel, docetaxel, and everolimus. The rapamycin, paclitaxel, docetaxel, and everolimus described above include their analogs and/or derivatives as long as the analogs and/or derivatives have equivalent drug activity to the original. For example, paclitaxel and docetaxel are in an analog relation. Rapamycin and everolimus are in a derivative relation. Among them, paclitaxel is more preferable.

The additive constitutes the additive layer 41 on the balloon 30. The additive contains a water-soluble low molecular weight compound. A molecular weight of the water-soluble low molecular weight compound is 50 to 2000, preferably 50 to 1000, more preferably 50 to 500, and still more preferably 50 to 200. An amount of the water-soluble low molecular weight compound is preferably 10 to 5000 parts by mass, more preferably 50 to 3000 parts by mass, and still more preferably 100 to 1000 parts by mass with respect to 100 parts by mass of the water-insoluble drug. Examples of a constituent material of the water-soluble low molecular weight compound include serine ethyl ester, saccharides such as glucose, sugar alcohols such as sorbitol, citrate ester, polysorbate, polyethylene glycol, urea, a water-soluble polymer, a contrast agent, amino acid ester, glycerol esters of a short-chain monocarboxylic acid, a pharmaceutically acceptable salt, a surfactant, and any mixture of two or more of them. The water-soluble low molecular weight compound is characterized by having a hydrophilic group and a hydrophobic group and being dissolved in water. The water-soluble low molecular weight compound is preferably a non-swelling water-soluble low molecular weight compound or hardly swelling water-soluble low molecular weight compound. The additive containing the water-soluble low molecular weight compound is effective to uniformly disperse the water-insoluble drug on the surface of the balloon 30. It is preferable that the additive constituting the additive layer 41 is not hydrogel. The additive layer 41 contains a low molecular weight compound, to thereby rapidly dissolve the additive layer without inflating when the additive layer is in contact with an aqueous solution. Furthermore, the additive layer 41 is easily dissolved at the time of inflating the balloon 30 in the blood vessel, such that an effect of easily releasing crystal particles of the water-insoluble drug on the surface of the balloon 30 and increasing an adhesive amount of the drug crystal particles to the blood vessel, is provided. In a case where the additive layer 41 is a matrix formed of a contrast agent such as Ultravist (registered trademark), the crystal particles are embedded in the matrix, and the crystals are not produced to extend from the balloon 30 toward outside of the matrix. Accordingly, the elongated body 42 in the present embodiment extends from the surface of the balloon 30 toward the surface of the additive layer 41.

The water-soluble low molecular weight compound has a molecular weight of 50 to 2000, and is dissolved at an amount of 1 mg/mL or more in water, preferably dissolved at an amount of 5 mg/mL or more in water, more preferably dissolved at an amount of 10 mg/mL or more in water, still more preferably dissolved at an amount of 33 mg/mL or more in water, and preferably dissolved in water without inflating. It is preferable that the water-soluble low molecular weight compound is not hydrogel. It is preferable that the water-soluble low molecular weight compound is not a polymer and a water-insoluble polymer. It is preferable that the water-soluble low molecular weight compound is not polyethylene glycol (PEG) and water-soluble PEG (for example, polyethylene glycol 200-600).

The solubility of a substance can be defined as a degree of dissolution within 30 minutes at 20° C. For example, the solubility of a substance can be defined by an amount of solvent (e.g., an amount of water) required to dissolve 1 g (or 1 mL) of solute. In cases where the amount of solvent required to dissolve 1 g of solute is less than 1 mL, the solute may be regarded as extremely soluble in the solvent. In cases of extremely soluble solutes, the amount of dissolved solute is more than 1000 mg/m L. Examples of extremely soluble substances include sorbitol, urea, and glycerol. In cases where the amount of solvent required to dissolve 1 g of solute is 1 mL or more and less than 10 mL, the solute may be regarded as soluble in the solvent. In cases, of soluble solutes, the amount of dissolved solute may be more than 100 mg/mL and 1000 mg/mL or less. Examples of soluble substances include polysorbate, amino acid ester, polyethylene glycol 200-600, serine ethyl ester, a contrast agent (iopromide), and a water-soluble polymer. In cases case where the amount of solvent required to dissolve 1 g of solute is 10 mL or more and less than 30 mL, the solute may be regarded as slightly soluble in the solvent. In cases of slightly soluble solutes, the amount of dissolved solute may be more than 33 mg/mL and 100 mg/mL or less. Examples of slightly soluble substances include polyethylene glycol. In cases where the amount of solvent required to dissolve 1 g of solute is 30 mL or more and less than 100 mL, the solute may be regarded as sparingly soluble in the solvent. In cases of sparingly soluble solutes, the amount of dissolved solute may be more than 10 mg/mL and 33 mg/mL or less. In cases where the amount of solvent required to dissolve 1 g of solute is 100 mL or more and less than 1000 mL, the solute may be regarded as insoluble in the solvent. In cases of insoluble solutes, the amount of dissolved solute may be more than 1 mg/mL and 10 mg/mL or less. In cases where the amount of solvent required to dissolve 1 g of solute is 1000 mL or more and less than 10000 mL, the solute may be regarded as extremely insoluble in the solvent. In cases of extremely insoluble solutes, the amount of dissolved solute may more than 0.1 mg/mL and 1 mg/mL or less. In cases where the amount of solvent required to dissolve 1 g of solute is 10000 mL or more, the solute may be regarded as hardly soluble in the solvent. In cases of hardly soluble solutes, the amount of dissolved solute may be 0.1 mg/mL or less. Examples of hardly soluble substances include fatty acid ester of glycerol. The water-soluble substance may be a substance other than a substance which is "extremely insoluble" or a substance which is "hardly soluble". Specifically, the water-soluble substance may be selected from substances which are "extremely soluble", "soluble", "sparingly soluble" or "insoluble". In certain embodiments, the water-soluble substance may be selected from substances which are "extremely soluble", "soluble", and "sparingly soluble".

The organic solvent is not particularly limited, and examples thereof include tetrahydrofuran, acetone, glycerin, ethanol, methanol, dichloromethane, hexane, and ethyl acetate. In certain embodiments, the organic solvent is a mixture of some tetrahydrofuran, ethanol, and acetone.

Suitable mixtures of the organic solvent and water include, but are not limited to, a mixture of tetrahydrofuran and water, a mixture of tetrahydrofuran, ethanol, and water, a mixture of tetrahydrofuran, acetone, and water, a mixture of acetone, ethanol, and water, and a mixture of tetrahydrofuran, acetone, ethanol, and water.

Next, a method for forming crystals of the water-insoluble drug on the surface of a balloon 30 using the above-described balloon coating apparatus 60 will be described.

First, inflation fluid is supplied to the balloon 30 through the three-way stopcock which is connected to the proximal opening portion 27 of the balloon catheter 10. Next, the three-way stopcock is operated to seal the inflation lumen 23 in a state in which the balloon 30 is inflated and maintains the state in which the balloon 30 is inflated. The balloon 30 is inflated in a pressure (for example, 4 atmosphere) lower than a pressure (for example, 8 atmosphere) at the time of using the balloon in the blood vessel. The drug coating layer 40 can be formed on the surface of the balloon 30 without inflating the balloon 30, and in this case, it is not required to supply the inflation fluid to the balloon 30.

Next, the balloon catheter 10 is rotatably placed on the supporting table 70 in a state in which the dispensing tube 94 is not in contact with the surface of the balloon 30 and the hub 26 is interlocked with the rotating mechanism section 61.

Next, a position of the moving table 81 is adjusted to position the dispensing tube 94 to the balloon 30. Here, the dispensing tube 94 is positioned at the most distal side of the balloon 30 on which the drug coating layer 40 is formed. As an example, an extending direction (ejecting direction) of the dispensing tube 94 is a direction opposite to a rotation direction of the balloon 30. Therefore, the balloon 30 can be rotated only in a direction opposite to a direction in which the coating solution is ejected from the dispensing tube 94 at a position where the balloon comes into contact with the dispensing tube 94. This rotation in the direction opposite to the ejecting direction gives a physical stimulus to the coating solution, thereby promoting the formation of crystal nuclei of the drug crystal. The extending direction (ejecting direction) toward the opening portion 95 of the dispensing tube 94 is a direction opposite to a rotation direction of the balloon 30, such that the crystals of the water-insoluble drug formed on the surface of the balloon 30 are likely to be formed by including a morphological form which includes the plurality of elongated bodies 42 and each have an independent long axis. The extending direction of the dispensing tube 94 may not be the direction opposite to the rotation direction of the balloon 30. Thus, the extending direction of the dispensing tube can be the same as the direction opposite to the rotation direction of the balloon or a direction perpendicular to the surface of the balloon 30.

Next, the coating solution is supplied to the dispensing tube 94 while adjusting the feeding amount by the liquid delivering pump 93, and the balloon catheter 10 is rotated by the rotating mechanism section 61. Furthermore, the moving table 81 is moved, thereby gradually moving the dispensing tube 94 to a proximal direction along the axial direction of the balloon 30. The dispensing tube 94 is moved relatively to the balloon 30, such that the coating solution ejected from the opening portion 95 of the dispensing tube 94 is applied to an outer circumferential surface of the balloon 30 while drawing a spiral.

The moving speed of the dispensing tube 94 is not particularly limited, and for example, 0.01 to 2 mm/sec, preferably 0.03 to 1.5 mm/sec, and more preferably 0.05 to 1.0 mm/sec. The ejecting speed of the coating solution from the dispensing tube 94 is not particularly limited, and for example, 0.01 to 1.5 μL/sec, preferably 0.01 to 1.0 μL/sec, and more preferably 0.03 to 0.8 μL/sec. The rotational speed of the balloon 30 is not particularly limited, and for example, the rotational speed thereof is 10 to 300 rpm, preferably 30 to 250 rpm, and more preferably 50 to 200 rpm. The diameter of the balloon 30 at the time of applying the coating solution is not particularly limited, and for example, the diameter thereof is 1 to 10 mm and preferably 2 to 7 mm.

Thereafter, the organic solvent containing the coating solution which is applied to the surface of the balloon 30 is volatilized earlier than water. Therefore, the organic solvent is volatilized in a state in which the water-insoluble drug, the water-soluble low molecular weight compound, and water remain on the surface of the balloon 30. As such, when the organic solvent is volatilized in a state in which water remains, the water-insoluble drug is precipitated in the water-soluble low molecular weight compound containing water, the crystals gradually grow from crystal nuclei, and the morphological drug crystals including the plurality of elongated bodies 42 in which the crystals each have an independent long axis are formed on the surface of the balloon 30. After the organic solvent is volatilized and the drug crystals are precipitated as the plurality of elongated bodies 42, water evaporates more slowly than the organic solvent, and the additive layer 41 containing the water-soluble low molecular weight compound is thus formed. A time when water evaporates is appropriately set depending on a type of drug, a type of water-soluble low molecular weight compound, a type of organic solvent, a ratio of material, an amount of application of the coating solution, and the like, and for example, the time is about 1 to 600 seconds.

By moving the dispensing tube 94 to the axial direction of the balloon 30 while rotating the balloon 30, the drug coating layer 40 is gradually formed on the surface of the balloon 30 toward the axial direction. After the drug coating layer 40 including elongated bodies 42 and the additive layer 41 is entirely formed in the range of the balloon 30 to be coated, the rotating mechanism section 61, the moving mechanism section 80, and the applying mechanism section 90 are stopped.

Thereafter, the balloon catheter 10 is separated from the balloon coating apparatus 60 and completes the coating of the balloon 30.

Next, a balloon folding apparatus will be described. The balloon folding apparatus is an apparatus capable of folding the balloon 30 so as to be wound around the inner tube 22.

Figure 6:
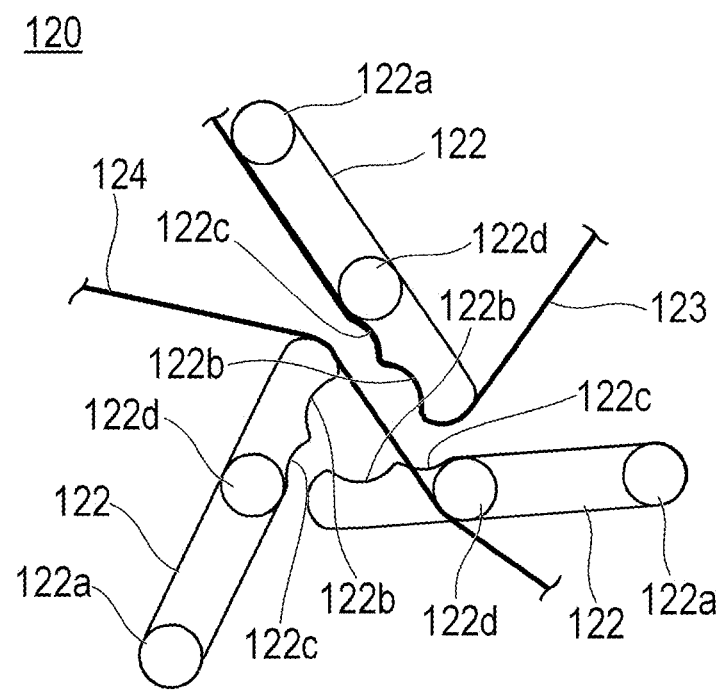
FIG. 6 is a front view illustrating blades of a pleating section.
Figure 7:
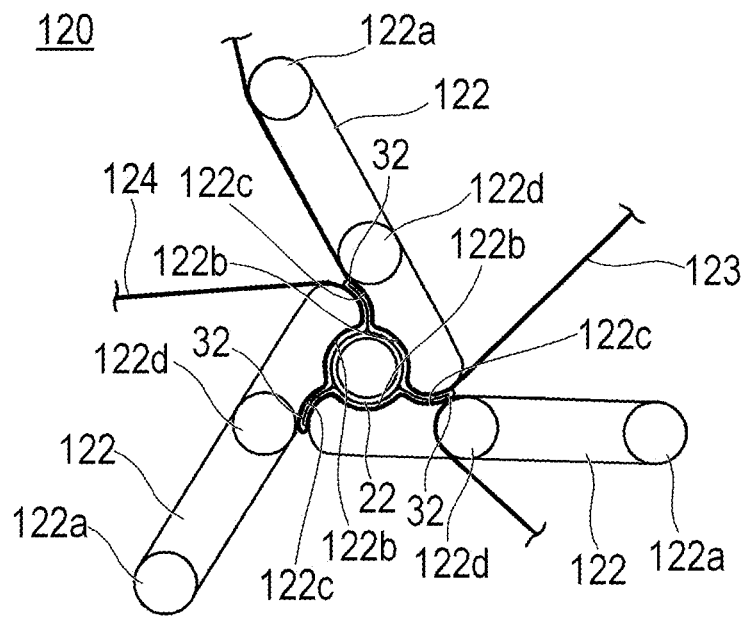
FIG. 7 is a front view illustrating a state in which the blades of the pleating section are rotated to form pleat portions on the balloon.
Figure 8:
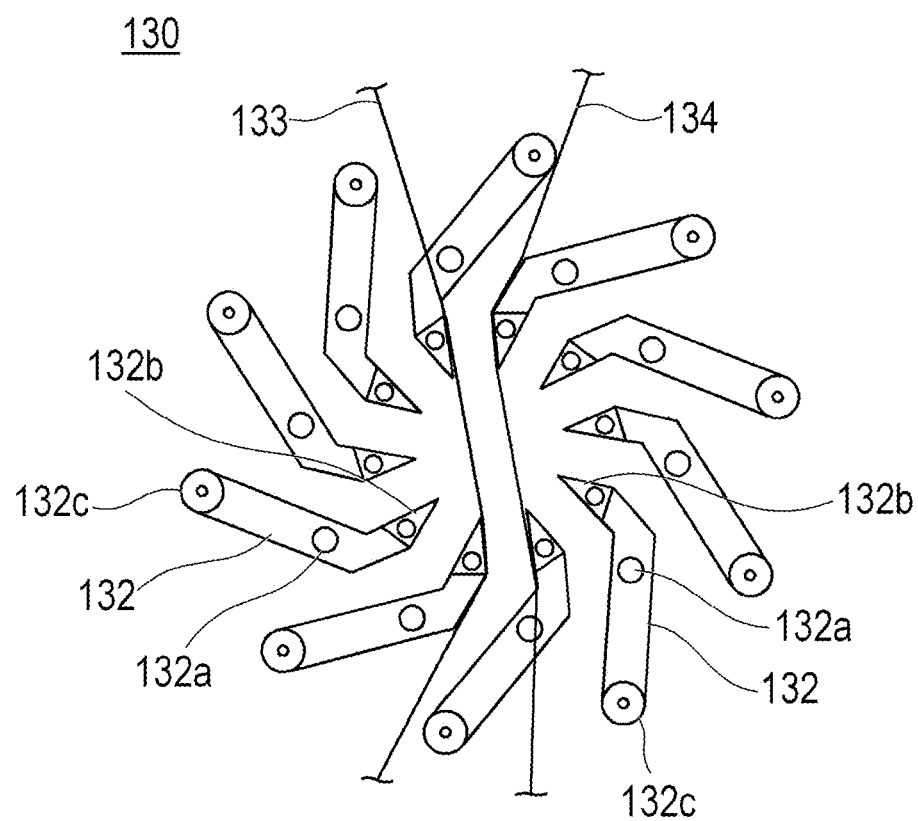
FIG. 8 is a front view illustrating blades of a folding section.
Figure 9:
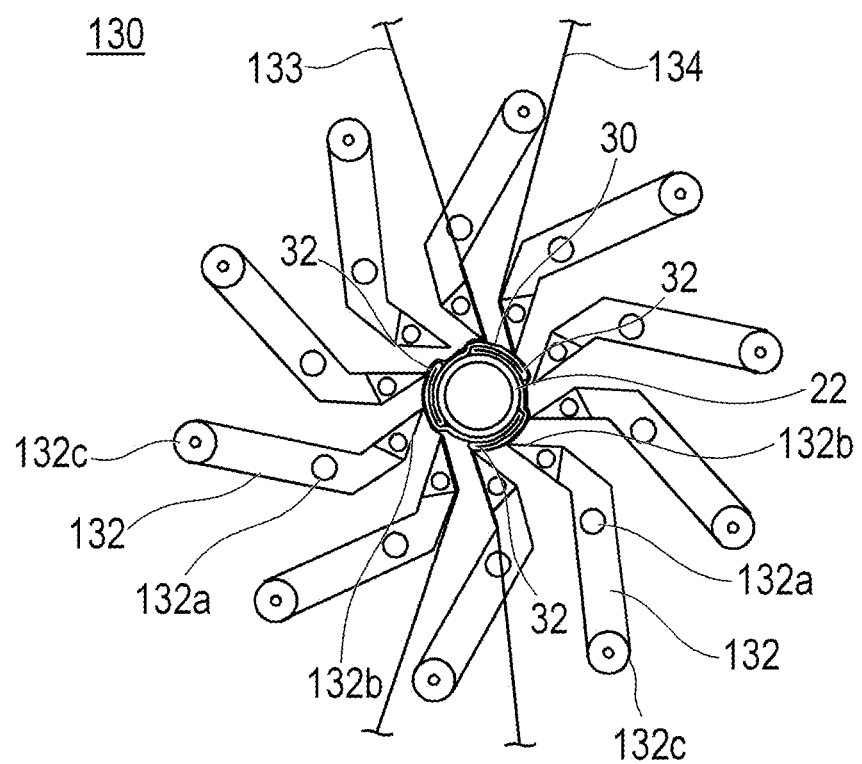
FIG. 9 is a front view illustrating a state in which the blades of the folding section are rotated to fold the pleat portions of the balloon.

The balloon folding apparatus includes a pleating section 120 illustrated in FIG. 6 and a folding section 130 illustrated in FIG. 8. In the pleating section 120, pleat portions (pleats) 32 protruding in the radial direction are formed in the balloon 30 as illustrated in FIG. 7. In the folding section 130, the pleat portions 32 formed in the balloon 30 can be folded by laying the blade portion in a circumferential direction as illustrated in FIG. 9. The pleat portions 32 formed in the balloon 30 is formed due to a fold extending the balloon 30 in a substantially axial direction, and when viewed in a cross section perpendicular to the axis of the balloon 30, the fold is formed so as to protrude from the long axis of the balloon 30 to the circumferential direction. The length of the pleat portions 32 in the axial direction does not exceed the length of the balloon 30. The length of the pleat portions or pleats 32 in a direction in which the pleats protrude from the catheter main body 20 in the circumferential direction, is about 1 to 8 mm. The number of pleat portions or pleats 32 is not particularly limited, and for example, 2 to 7, but in the present embodiment, the number of pleat portions is 3.

First, a pleating section 120 will be described. As illustrated in FIGS. 6 and 7, the pleating section 120 has three blades 122 therein. Each of the blades 122 is a plate-shaped member in which a cross-sectional shape at each position of the balloon catheter 10 to be inserted along the axial direction is formed into the same shape. Each of the blades 122 is disposed to be 120 degrees with respect to a center position through which the balloon 30 is inserted. That is, each of the blades 122 is disposed in the circumferential direction at every equal angle. The blade 122 has a rotating center portion 122a in the vicinity of an outer circumferential end of the blade and can be rotated around the rotating center portion 122a. In addition, the blade 122 has a movable pin 122d provided on an inner circumferential side from the rotating center portion 122a and extending in the axial direction. The movable pin 122d can be movable around the rotating center portion 122a. When the movable pin 122d is moved, each of the blades 122 is rotated around the rotating center portion 122a. The three blades 122 are rotated, such that a spatial region of the center portion surrounded by the blade 122 can be narrowed. The number of blades 122 is not particularly limited as long as the number of blades is 2 or more.

The blades 122 have a substantially arc-shaped first shape forming section 122b and a substantially arc-shaped second shape forming section 122c on an inner circumferential end opposite to the rotating center portion 122a. The first shape forming section 122b is attached to the surface of the balloon 30 into which the pleating section 120 is inserted in accordance with the rotation of the blades 122, such that the pleat portions or pleats 32 protruding in the radial direction can be formed in the balloon 30. The second shape forming section 122c is attached to a part of the pleat portions formed in the balloon 30 in accordance with the rotation of the blades 122, such that the pleat portions 32 can be curved in a predetermined direction. In addition, the pleating section 120 has a heater (not illustrated) for heating the blades 122.

In the blades 122, a first film 123 and a second film 124 which are made of a resin are supplied so as to flow in one direction. The first film 123 is coupled to a surface of the blade 122 disposed at an upper portion of the pleating section. The second film 124 is coupled to the other two blades 122 disposed at a lower portion of the pleating section. Accordingly, the center position of the pleating section 120 through which the balloon 30 is inserted is surrounded by the first film 123 and the second film 124.

When the balloon 30 is inserted into the pleating section 120 and the blades 122 are rotated to form the pleat portions or pleats 32 in the balloon 30, the first film 123 and the second film 124 protect so that the balloon 30 does not directly come into contact with the surface of the blades 122. After the pleat portions or pleats 32 of the balloon 30 are formed, the first film 123 and the second film 124 are moved by a predetermined length. That is, a part in which the first film 123 and the second film 124 come into contact with the balloon 30 once does not come into contact with the balloon 30 again, and a new part is supplied to the center position of the pleating section 120 every time a balloon 30 is inserted.

First, the folding section 130 will be described. As illustrated in FIGS. 8 and 9, the folding section 130 has ten blades 132. Each of the blades 132 is a plate-shaped member in which a cross-sectional shape at each position of the balloon catheter 10 to be inserted along the axial direction is formed into the same shape. Each of the blades 132 is disposed to be 36 degrees with respect to a center position through which the balloon is inserted so that each blade extends from a center position forming 36 degrees to the next blades. That is, each of the blades 132 is disposed in the circumferential direction at equal angular intervals. Each blade 132 has a rotating center portion 132a in the vicinity of a substantial center of the blade and can be rotated around the rotating center portion 132a. In addition, each of the blades 132 has a movable pin 132c provided in the vicinity of a substantial outer circumferential end of the blade and extending in the axial direction. The movable pin 132c can be movable around the rotating center portion 132a. When the movable pin 132c is moved, each of the blades 132 is rotated around the rotating center portion 132a. The ten blades 132 are rotated, such that a spatial region of the center portion surrounded by the blade 132 can be narrowed. The number of blades 132 is not particularly limited to 10.

Each blade 132 has a tip side or tip end portion that is curved or angled and a tip portion 132b that has a sharp shape or forms a point. As the blade 132 rotates, the tip portion 132b comes into contact with the surface of the balloon 30 inserted into the folding section 130 so that the pleat portions or pleats 32 formed in the balloon 30 can be folded so as to be laid in the circumferential direction. In addition, the folding section 130 has a heater (not illustrated) for heating the blades 132.

In the folding section 130, a third film 133 and a fourth film 134 which are made of a resin are supplied so as to flow in one direction. The third film 133 and the fourth film 134 are disposed to face each other, such that the third film and the fourth film sandwich a central spatial region surrounded by the blades 132. When the balloon 30 is inserted into the folding section 130, the third film 133 and the fourth film 134 protect so that the balloon 30 does not directly come into contact with the surface of the blades 132.

Next, a method for folding the balloon 30, in which the drug coating layer 40 is formed on the surface by the balloon coating apparatus 60 using the balloon folding apparatus, will be described.

First, in order to form the pleat portions or pleats 32 in the balloon 30, the balloon 30 of the balloon catheter 10 is inserted into the pleating section 120 illustrated in FIG. 6. The blades 122 of the pleating section 120 are heated. Next, as illustrated in FIG. 7, the blades 122 are rotated. As a result, the first shape forming section 122b of each of the blades 122 approaches, and a center region between the blades 122 is thus narrowed. According to this, the balloon 30 inserted into the center region between the blades 122 is pressed against the inner tube 22 by the first shape forming section 122b. A part of the balloon 30 which is not pressed by the first shape forming section 122b is pushed out to a clearance between the tip portion of the blade 122 and the second shape forming section 122c of the blade 122 adjacent to the corresponding blade 122, and the pleat portions 32 curved in one side is thus formed. Since the balloon 30 is heated to about 50 to 60 degrees by the blades 122, the formed pleat portions 32 can maintain their shape as is. Thus, the three pleat portions 32 in the circumferential direction are formed in the balloon 30.

In this case, the surface coming into contact with the balloon 30 of each of the blades 122 is covered with the first film 123 and the second film 124, such that the balloon 30 does not directly come into contact with the surface of the blades 122. After the pleat portions or pleats are 32 formed in the balloon 30, the blades 122 rotated so as to return to their original position, and the balloon 30 is withdrawn from the pleating section 120. In a pleating process, since a volume inside the balloon 30 is reduced, it is preferable that the three-way stopcock is adjusted in accordance with the reduction of the volume and the inflation fluid is discharged to the outside to deflate the balloon 30. Thus, it is possible to prevent the excessive force from being applied to the balloon 30.

Figure 10A:
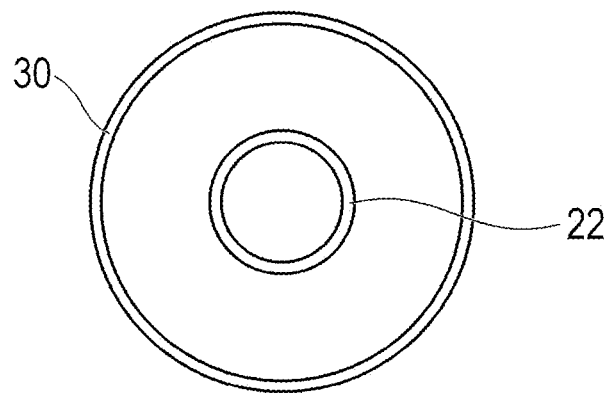
FIGS. 10A-10C are cross-sectional views illustrating the balloon folded by a balloon folding apparatus.
Figure 10B:
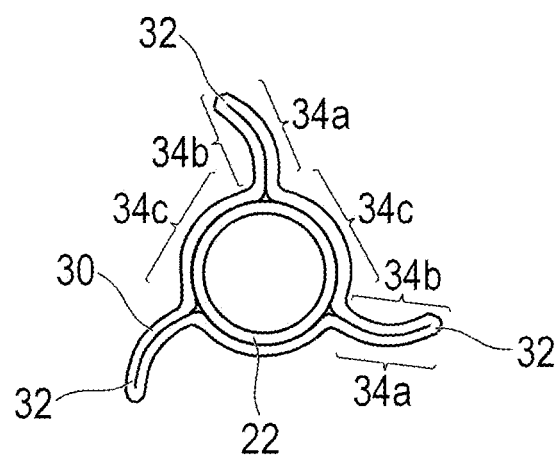

As illustrated in FIG. 10A, the balloon 30 has a cross section with a substantial circular shape in a state where the inflation fluid is injected inside the balloon. By forming the protruding pleat portions or pleats 32 from this state, as illustrated in FIG. 10B, the balloon 30 includes blade outer portions 34a pressed against the second shape forming section 122c and constituting an outer surface of the pleat portions 32, blade inner portions 34b pressed against the tip portion of the blade 122 and constituting an inner surface of the pleat portions 23, and intermediate portions 34c located between the blade outer portion 34a and the blade inner portion 34b and pressed against the first shape forming section 122b.

Next, the balloon catheter 10 is withdrawn from the pleating section 120. Next, the balloon 30 of the balloon catheter 10 is inserted into the folding section 130 illustrated in FIG. 8. The blades 132 of the folding section 130 are heated to about 50 to 60 degrees.

After the balloon 30 in which the pleat portions 32 are formed is inserted into the folding section 130, the blades 132 are rotated as illustrated in FIG. 9. As a result, the tip portion 132b of each of the blades 132 approaches to each other, and a center region between the blades 132 is thus narrowed. According to this, the balloon 30 inserted into the center region between the blades 132 is in a state in which the pleat portions 32 are laid in the circumferential direction by the tip portion 132b of each of the blades 132. Since the blade 132 is heated in advance before inserting the balloon 30 and the balloon 30 is heated by the blade 132, the pleat portions or pleats 32 which are laid in the circumferential direction can maintain their shape by the blades 132. Here, the surface coming into contact with the balloon 30 of each of the blades 132 is covered with the third film 133 and the fourth film 134, such that the balloon 30 does not directly come into contact with the surface of the blades 132.

Figure 10C:
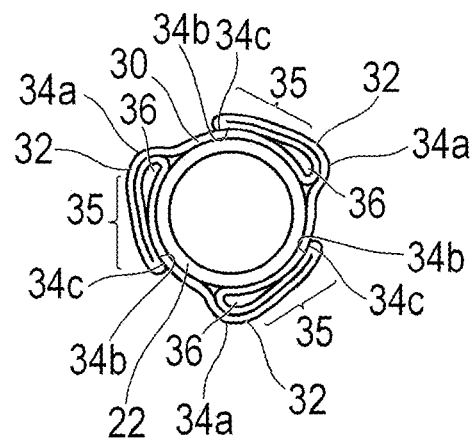

When the pleat portions 32 of the balloon 30 are folded, as illustrated in FIG. 10C, the blade inner portion 34b and the intermediate portion 34c come into contact with each other in an overlapped manner, and an overlapped portion 35 in which the surfaces of the balloon face and overlap each other is formed. Then, a part of the intermediate portion 34c and the blade outer portion 34a are exposed to the outside without covering the blade inner portion 34b. In addition, a root side space portion 36 is formed between a root portion of the pleat portion 32 and the intermediate portion 34c in a state in which the balloon 30 is folded. In a region of the root side space portion 36, a minute clearance is formed between the pleat portion 32 and the intermediate portion 34c. On the other hand, a region of the tip side from the root side space portion 36 of the pleat portion 32 is in close in contact with the intermediate portion 34c.

After the pleat portions 32 of the balloon 30 are folded, the blades 132 are rotated so as to return to its original position. Next, the balloon 30 is withdrawn from the folding section 130. Thus, the folding of the balloon 30 is completed.

Next, an effect of the drug coating layer 40 according to the first embodiment will be described.

As illustrated in FIG. 3, in the drug coating layer 40 on the surface of the balloon 30, the water-soluble additive layer 41 is provided so as to fill a space between the elongated bodies 42. That is, the additive layer 41 is embedded between the elongated bodies 42. Therefore, in a process of forming and folding the pleat portions 32 in the balloon 30 by the pleating section 120 and the folding section 130, although a force is applied to the drug coating layer 40, the elongated body 42 is protected by the additive layer 41 and the folding of the balloon is thus prevented. Therefore, when the folded balloon 30 is inserted into the blood vessel, the drug crystals fall-off from the folded elongated body 42 and the crystals which have fallen-off can be prevented from flowing out in the blood at the time of delivering the drug crystals to the balloon 30. Thus, it is possible to prevent the fallen-off drug crystals from having an undesirable effect on the living body.

After the balloon 30 is disposed at the stenosed site, as illustrated in FIGS. 1 and 2, the inflation fluid from the proximal opening portion 27 of the hub 26 is injected in a predetermined amount using an inflator, a syringe, or the like, and the inflation fluid is fed into the balloon 30 through the inflation lumen 23. Thus, the folded balloon 30 is inflated. Consequently, the drug coating layer 40 provided on the surface of the balloon 30 comes into contact with the stenosed site. When the drug coating layer 40 is pressed against to a biological tissue, the drug is delivered to the living body while dissolving the additive layer 41 which is the water-soluble low molecular weight compound contained in the drug coating layer 40. In addition, when the balloon 30 is inflated, cracks are generated in the additive layer 41 and the additive layer is easily thus dissolved, and the elongated bodies 42 which are the drug crystals are easily released from the additive layer 41.

When the inflation fluid is sucked from the proximal opening portion 27 of the hub 26 and discharged from the inside of the balloon 30, the balloon 30 is deflated and folded. Thus, the balloon catheter 10 can be extracted from the blood vessel.

As described above, the drug coating layer 40 according to an embodiment may be a drug coating layer 40 formed on the surface of the balloon 30, and the drug coating layer includes the plurality of elongated bodies 42 which are crystals of the water-insoluble drug and each have a long axis (elongated axis or longitudinal axis) extending from the surface of the balloon 30 at various lengths and angles, and a water-soluble additive layer 41 which is provided between the outer surface 51 of the aggregate 50 of the plurality of elongated bodies 42 and the surface of the balloon 30 so as to fill spaces between the elongated bodies 42, the outer surface being located outside the aggregate 50 and having an unevenness connecting the plurality of tip ends 46 and side surfaces 43 of the elongated bodies 42 to each other, in which the tip ends 46 of the elongated body 42 slightly protrude from the additive layer 41, and the side surfaces 43 and/or the tip surfaces 47 of the elongated body 42 are exposed on the surface of the additive layer 41. The tip end 46 of the elongated body 42 can slightly protrude from the additive layer 41.

In the drug coating layer 40 configured as described above, since the tip end of the elongated body 42 slightly protrudes from the additive layer 41, the breakage of the elongated body 42 on the surface of the balloon 30 can be prevented and the elongated body 42 can be maintained in an appropriate shape in order to act on the living body. In addition, although a force is applied to the drug coating layer 40 when the balloon 30 is folded, the elongated body 42 is protected by the additive layer 41 and the folding of the balloon is thus prevented. Therefore, when the folded balloon 30 is inserted into the blood vessel, the drug crystals are fallen off from the folded elongated body 42 and the fell-off drug crystals can be prevented from flowing out in the blood at the time of delivering the drug crystals to the balloon 30. Thus, it is possible to prevent the fell-off drug crystals from having an undesirable effect on the living body. Furthermore, since the side surface 43 and/or the tip surface 47 of the elongated body 42 is exposed on the surface of the additive layer 41, the additive layer 41 does not interfere with transferability in blood vessel of the elongated body 42 which is a drug, without excessively embedding the elongated body 42 in the additive layer 41.

The additive in the additive layer 41 protects the drug crystals while moving in the blood vessel. Alternatively, when the balloon 30 is inflated in a target lesion, the additive layer 41 for protecting the crystals in a product package form comes into contact with the blood, such that the additive is rapidly dissolved. As a result, an effect that the drug crystals come into contact with a blood vessel wall is shown.

The water-insoluble drug contains at least one selected from the group consisting of rapamycin, paclitaxel, docetaxel, and everolimus. Thus, it is possible to properly prevent restenosis of the stenosed site in the blood vessel due to the elongated body 42 which is a drug crystal.

Second Embodiment

A drug coating layer 140 according to a second embodiment differs from the drug coating layer according to the first embodiment in that the drug coating layer 140 includes a first additive layer 141 and a second additive layer 142 as illustrated in FIG. 11. Features in this embodiment that function the same as features described above are identified by the same reference numeral and a detailed description of such features is not repeated.

Figure 11A:
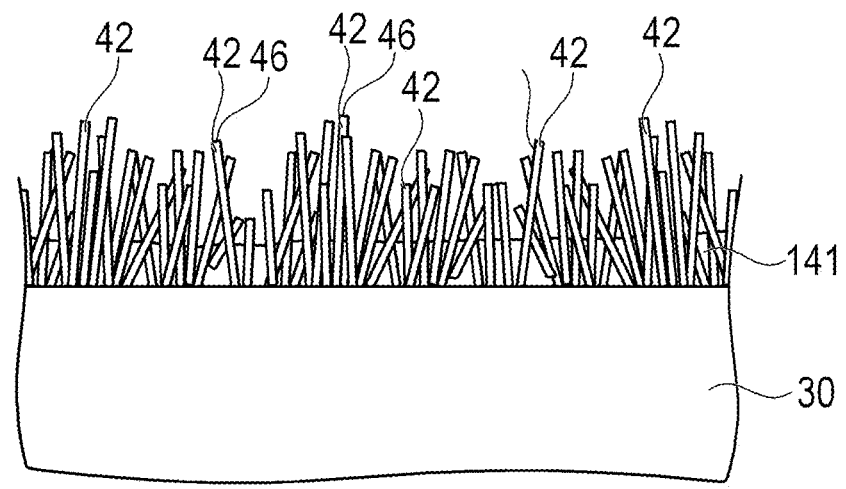
FIGS. 11A and 11B are cross-sectional views for illustrating a process of forming a drug coating layer according to a second embodiment.

According to the second embodiment, the first additive layer 141 and the second additive layer 142 of the drug coating layer 140 are formed on a surface of the balloon 30 by different processes. As illustrated in FIG. 11A, the first additive layer 141 may include a first coating solution supplied to the surface of the balloon 30 using the balloon coating apparatus 60 (see FIG. 4). The first coating solution contains a water-insoluble drug, a first water-soluble additive, an organic solvent, and water. The first coating solution can be the same as the coating solution in the first embodiment, and may be different from each other. After the first coating solution is supplied to the surface of the balloon 30, an organic solvent and water are volatilized, such that a plurality of elongated bodies 42 which are crystals of the water-insoluble drug and each have an independent long axis and the first additive layer 141 are formed on the surface of the balloon 30. The elongated body 42 protrudes from the first additive layer 141. A length of a part of the elongated body 42 protruding from the surface of the first additive layer 141 toward the outside is not particularly limited, and for example, the length thereof is more than 1 μm and 10 μm or less. The elongated body 42 is embedded in the first additive layer 141 at a length of equal to or longer than half of the total length of the elongated body 42. The elongated body 42 embedded in the first additive layer 141 without any exposed portion is also possible.

Figure 11B:
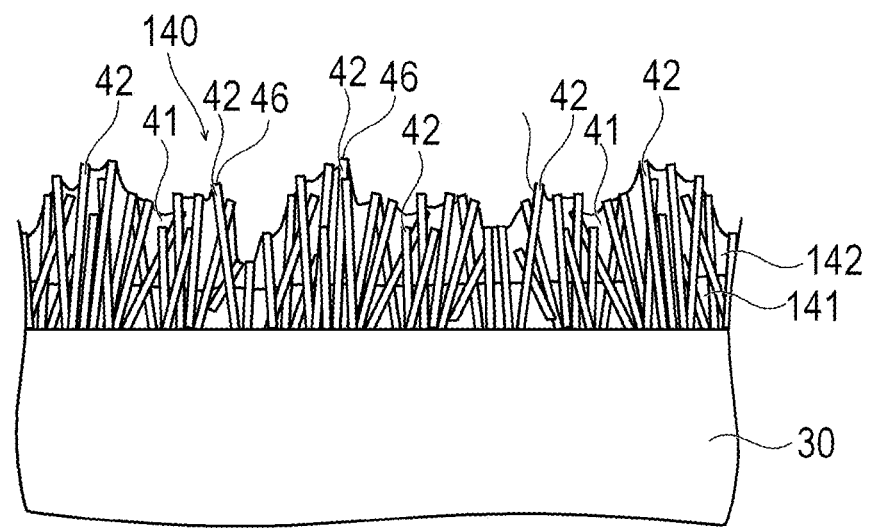

Next, a second coating solution containing the second water-soluble additive and a solvent is supplied to the surfaces of the first additive layer 141 and the elongated body 42. The second coating solution can be supplied by the same method as the first coating solution, using the above-described balloon coating apparatus 60 (see FIG. 4). The second coating solution may be supplied by other methods such as dipping, spraying, and dropping. The second coating solution uses a solvent that does not redissolve the elongated body 42. The solvent is, for example, water or ethanol containing water. As illustrated in FIG. 11B, when the solvent supplied to the surfaces of the first additive layer 141 and the elongated body 42 evaporates, the second additive layer 142 containing the second water-soluble additive is formed so as to fill a space between the elongated bodies 42 protruding from the first additive layer 141. The second water-soluble additive may be the same as or different from the first water-soluble additive. The second coating solution does not contain the drug. The second water-soluble additive may contain the drug. The second coating solution may contain an organic solvent as long as the elongated body 42 is not redissolved in some extent. A length of a part of the elongated body 42 protruding from the surface of the second additive layer 142 toward the outside is not particularly limited, and for example, the length thereof is 0 to 1 μm (slightly protrude). The elongated body 42 which has no exposed portion embedded in the second additive layer 142 also exists.

In cases in which the additive in the first coating solution (additive in the first additive layer 141) is in a state from an extremely soluble additive to a slightly soluble additive, the additive is rapidly dissolved when the balloon 30 is inflated in the target lesion, and thus the drug crystals can be directly adhered to the blood vessel wall. An additive in the second coating solution (additive in the second additive layer 142) protects the drug crystals in the balloon when the balloon 30 is folded. Therefore, the additive in the second coating solution may have a high solubility, but if the solubility means that the additive in the second coating solution is insoluble, slightly soluble, or sparingly soluble as compared with the additive in the first coating solution, it is possible to reduce the damage of the drug crystals while being transported in the blood vessel.

Cases in which the additive in the first coating solution is more soluble than the additive in the second coating solution include cases wherein the additive in the first coating solution is extremely soluble, e.g. having a solubility more than 1000 mg/mL, and the additive in the second coating solution is slightly soluble, e.g. having a solubility more than 33 mg/mL and 100 mg/mL or less. Other cases in which the additive in the first coating solution is more soluble than the additive in the second coating solution include cases wherein the additive in the first coating solution is slightly soluble, e.g. having a solubility more than 33 mg/mL and 100 mg/mL or less, and the additive in the second coating solution is sparingly soluble, e.g. having a solubility more than 10 mg/mL and 33 mg/mL or less.

In cases in which the additive in the first coating solution (additive in the first additive layer 141) is sparingly soluble and the additive in the second coating solution (additive in the second additive layer 142) is soluble, the additive is dissolved from an upper layer portion of the surface of the balloon 30 (side coming into contact with the blood vessel) when the balloon 30 is inflated. Therefore, since the drug crystals are adhered to the blood vessel while maintaining an angle of the elongated body 42 with respect to the balloon 30, the drug crystals can be prevented from falling off from the balloon.

Cases in which the additive in the second coating solution is more soluble than the additive in the first coating solution include cases wherein the additive in the first coating solution is slightly soluble, e.g. having a solubility more than 33 mg/mL and 100 mg/mL or less and wherein the additive in the second coating solution is soluble, e.g. having a solubility more than 100 mg/mL and 1000 mg/mL or less. Other cases in which the additive in the second coating solution is more soluble than the additive in the first coating solution include cases wherein the first coating solution is sparingly soluble, e.g. having a solubility more than 10 mg/mL and 33 mg/mL or less and wherein the additive in the second coating solution is slightly soluble, e.g. having a solubility more than 33 mg/mL and 100 mg/mL or less.

In a certain embodiment, the drug coating layer 140 includes the first additive layer 141 provided on the surface of the balloon 30, and the second additive layer 142 provided to cover the outside of the first additive layer 141 and fill a space between the elongated bodies 42 protruding from the first additive layer 141. Thus, the breakage of the elongated body 42 can be prevented by the second additive layer 142 while properly holding the elongated body 42 on the surface of the balloon 30 by the first additive layer 141.

In addition, the first additive layer 141 and the second additive layer 142 contain the same or different water-soluble low molecular weight compounds. Thus, the first additive layer 141 and the second additive layer 142 are rapidly dissolved in the blood vessel, and thus does not interfere with the transferability in blood vessel of the elongated body 42 which is a drug. In a case where the first additive layer 141 and the second additive layer 142 contain the different water-soluble low molecular weight compounds, the additive which is likely to form the elongated body 42 on the surface of the balloon 30 can be used for the first additive layer 141 and the additive which is likely to prevent the breakage of the elongated body 42 can be used for the second additive layer 142. In a case where the first additive layer 141 and the second additive layer 142 contain the same water-soluble low molecular weight compound, the same additive may be used for the second additive layer 142 after the additive which is likely to form the elongated body 42 on the surface of the balloon 30 is used for the first additive layer 141, or the second additive layer 142 may be formed simultaneously when the first additive layer is formed. Examples of a combination of the first additive layer 141 and the second additive layer 142 include but are not limited to serine ethyl ester and polysorbate, polyethylene glycol and sorbitol, serine ethyl ester and glucose, serine ethyl ester and polyethylene glycol, polysorbate and sorbitol, and serine ethyl ester and citrate ester.

A method for forming the drug coating layer 140 according to the second embodiment is a method for forming the drug coating layer 40 in which the plurality of elongated bodies 42 which are crystals of a water-insoluble drug and each have a long axis are formed on the surface of the balloon, and the method includes a step of supplying the first coating solution which contains the water-insoluble drug, the first water-soluble additive, an organic solvent, and water to the surface of the balloon 30 and evaporating the organic solvent and the water to form the first additive layer 141 containing the first water-soluble additive and the elongated bodies 42 protruding from the first additive layer 141, and a step of supplying the second coating solution which contains the second water-soluble additive and water to the first additive layer 141 and the elongated bodies 42 and evaporating the water to form the second additive layer 142 so as to fill a space between the elongated bodies 42 protruding from the first additive layer.

In an aspect of the method for forming the drug coating layer 140 configured as such, it is possible to securely form the first additive layer 141 and the elongated body 42 protruding from the first additive layer 141, using the appropriate amount of the first water-soluble additive. Thereafter, the second additive layer 142 is formed to fill the space between the elongated bodies 42, thereby preventing the breakage of the elongated bodies 42, which are the drugs, and maintaining the elongated bodies 42 an appropriate shape in order to act on the living body. When the amount of the first water-soluble additive is too large for the amount of drug during formation of the elongated body 42, the amount of drug to be crystallized is relatively small, and it is difficult to adjust the morphological form of the elongated body 42 extending from the surface of the balloon 30. Conversely, when the first additive layer 141 and the elongated body 42 are formed using an appropriate amount of the first water-soluble additive, thereby controlling and forming the elongated body 42 in a desired morphological form.

Figure 12A:
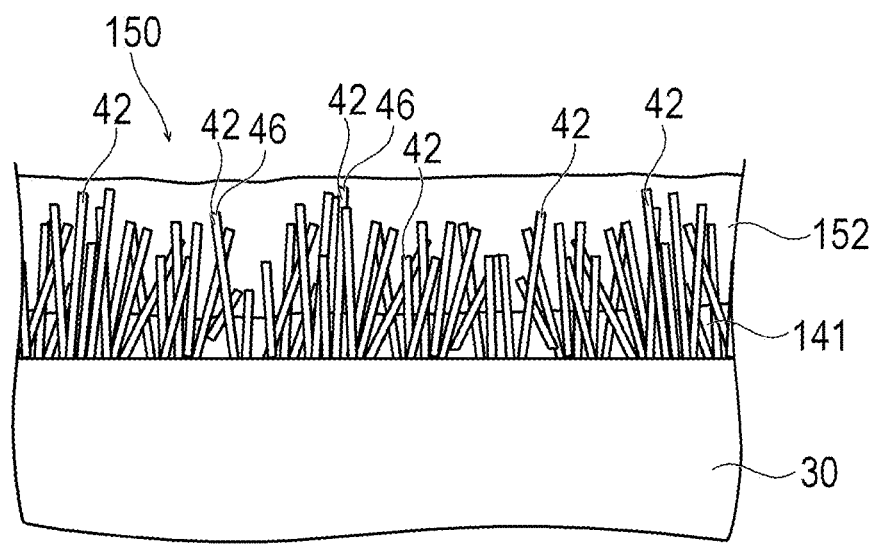
FIGS. 12A and 12B are cross-sectional views illustrating a modification example.

As in a modification of the embodiment depicted in FIG. 12A, a second additive layer 152 of a drug coating layer 150 may cover the first additive layer 141 and almost all the elongated bodies 42 protruding from the first additive layer 141. In this case, the tip end 46 of the elongated body 42 does not protrude from the second additive layer 152. The same reference signs will be given to elements having functions which are the same as those according to the above-described embodiment, and description thereof will be omitted.

Figure 12B:
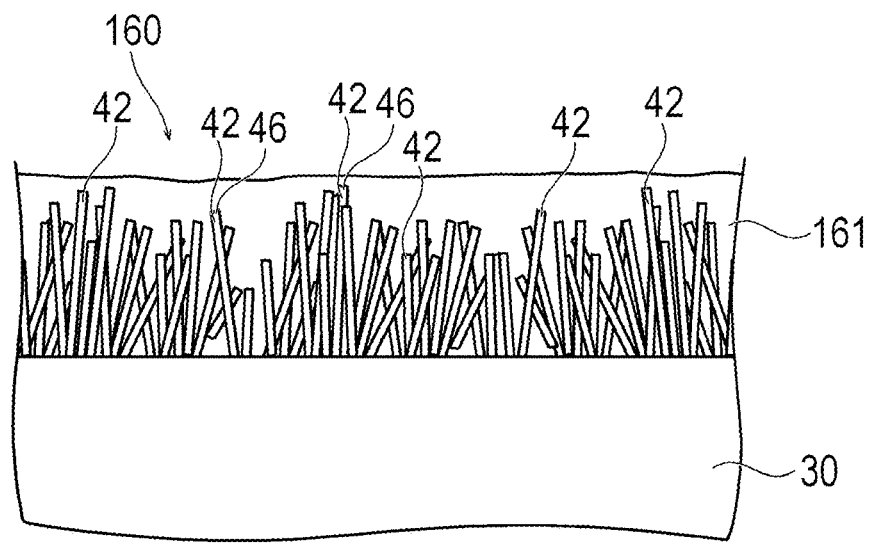

In addition, as in a modification of the embodiment depicted in FIG. 12B, an additive layer 161 of a drug coating layer 160 may be a single layer and cover almost all the elongated bodies 42. In this case, the tip end 46 of the elongated body 42 does not protrude from the additive layer 161. The same reference signs will be given to elements having functions which are the same as those according to the above-described embodiment, and description thereof will be omitted.

Figure 13:
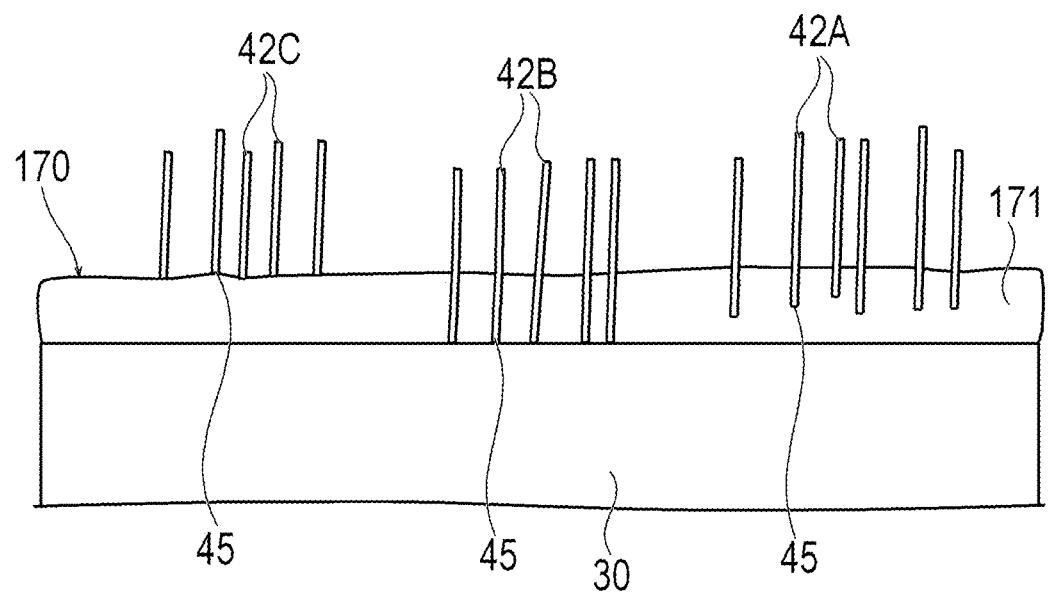
FIG. 13 is a cross-sectional view illustrating another example of the drug coating layer.

In addition, as in another modification example in FIG. 13, a drug coating layer 170 may have an additive layer 171, first elongated bodies 42A, second elongated bodies 42B, and third elongated bodies 42C. The first elongated body 42A extends from the inside of the additive layer 171 to the outside of the additive layer 171. The second elongated body 42B extends from an outer surface of the balloon 30 to the outside of the additive layer 171 by penetrating the additive layer 171. The third elongated body 42C extends from the outer surface of the additive layer 171 to an out-of-plane direction. The elongated body 42 may have only the first elongated body 42A. The elongated body 42 may have only the second elongated body 42B. The elongated body 42 may have the first elongated body 42A and the second elongated body 42B together.

The present invention is not limited only to the embodiment described above, and various modifications can be made by a person skilled in the art within the technical thought of the present invention. For example, the balloon catheter 10 according to the above-described embodiment may be a rapid exchange type balloon catheter or an over-the-wire type balloon catheter.

The drug coating layer formed on a surface of a balloon and methods of making the same have been described above. Examples of the drug coating layer formed on a surface of a balloon and methods of making the same are set forth below. The present invention is not limited to the configuration described in the following Examples.

EXAMPLES

Example 1

Figure 14:
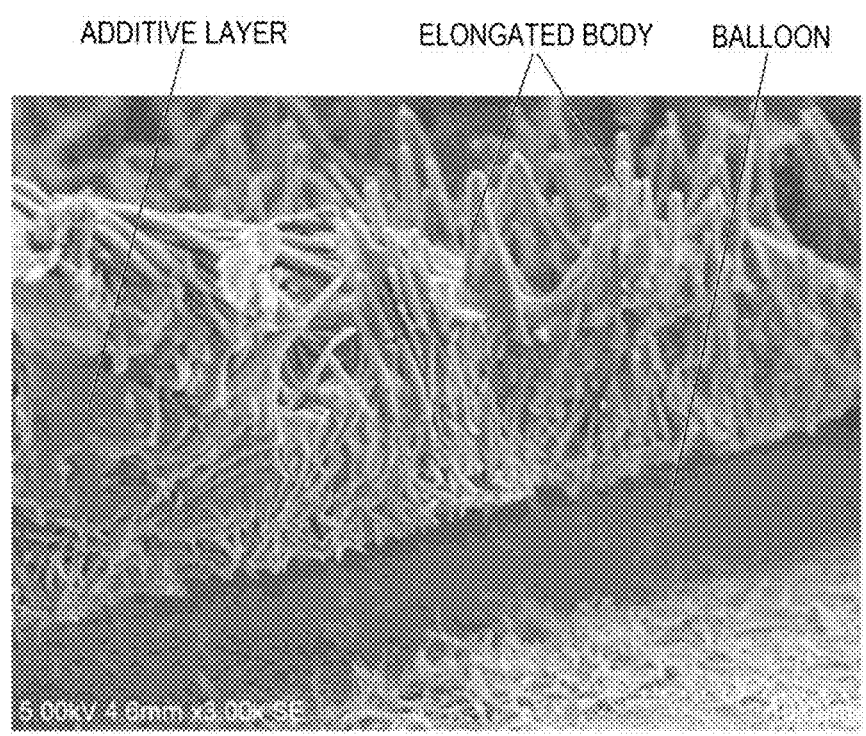
FIG. 14 is a photograph illustrating a drug coating layer in Example 1.

A drug coating layer including elongated bodies which are crystals of a water-insoluble drug and each have a long axis, a first additive layer, and the second additive layer was formed. A constituent material of the drug coating layer on the balloon in Example 1 was nylon 12, and a water-insoluble drug constituting the elongated body was paclitaxel. As the water-soluble additive, serine ethyl ester was used for the first additive layer and the same serine ethyl ester as the first additive layer was used for the second additive layer. A solvent of a first coating solution was tetrahydrofuran and acetone, and a solvent of a second coating solution was ethanol and water. An amount of a water-soluble low molecular weight compound was 500 parts by mass with respect to 100 parts by mass of the water-insoluble drug. FIG. 14 illustrates a photograph of the drug coating layer in Example 1.

The surface of the drug coating layer had an undulated shape in some extent. The surface of the drug coating layer was formed by the surface of the additive layer, a side surface and a tip surface of the elongated body which are embedded in the additive layer and located on a surface layer of the additive layer. It was confirmed that the tip end of the elongated body slightly protrudes from the additive layer.

Example 2

Figure 15:
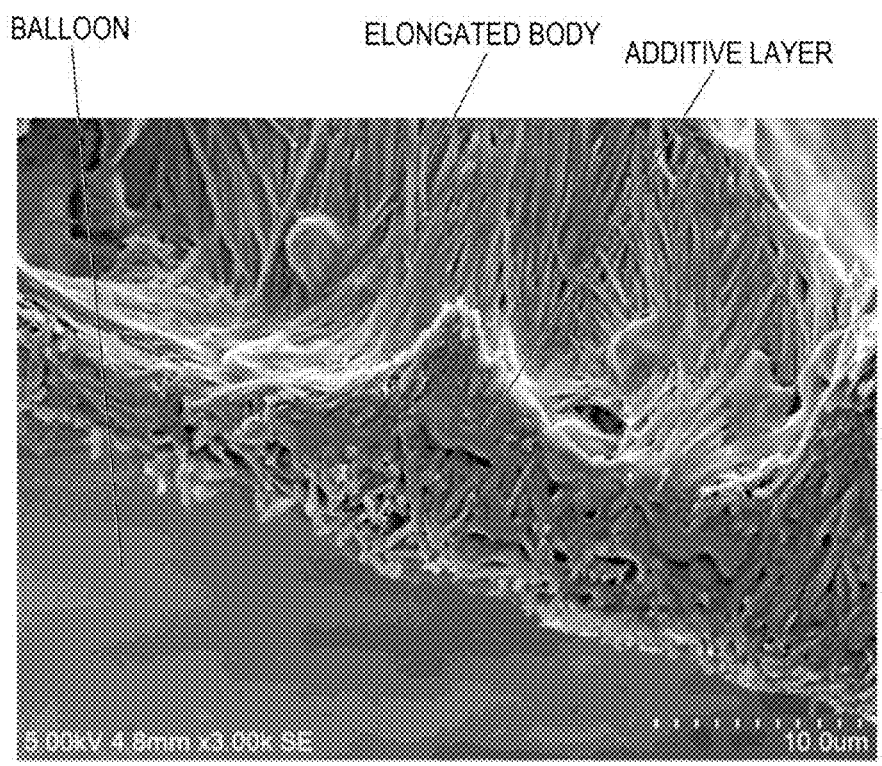
FIG. 15 is a photograph illustrating a drug coating layer in Example 2.

A drug coating layer including elongated bodies which are crystals of a water-insoluble drug and each have a long axis, a first additive layer, and the second additive layer was formed. Nylon 12 was used for a constituent material of the drug coating layer on the balloon in Example 2 and paclitaxel was used for a water-insoluble drug constituting the elongated body. As the water-soluble additive, a constituent material of the first additive layer used serine ethyl ester and a constituent material of the second additive layer used the same serine ethyl ester as the first additive layer. A solvent of a first coating solution was tetrahydrofuran and acetone, and a solvent of a second coating solution was ethanol and water. An amount of a water-soluble low molecular weight compound is 1000 parts by mass with respect to 100 parts by mass of the water-insoluble drug. FIG. 15 illustrates a photograph of the drug coating layer in Example 2.

The surface of the drug coating layer had a somewhat undulated shape. The surface of the drug coating layer was formed by the surface of the additive layer, a side surface and a tip surface of the elongated body which were embedded in the additive layer and located on a surface layer of the additive layer. It was confirmed that the tip end of the elongated body slightly protruded from the additive layer.

The detailed description above describes versions of a drug coating layer formed on a surface of a balloon and methods of making the same, representing examples of the inventive drug coating layer formed on a surface of a balloon and the inventive methods of making the same. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A drug coating layer formed on an outer surface of a balloon, the drug coating layer formed on the outer surface of the balloon comprising:
   a plurality of elongated bodies, the elongated bodies being crystals of a water-insoluble drug, the plurality of elongated bodies each possessing a longitudinal axis and extending in a direction away from the outer surface of the balloon, the plurality of elongated bodies extending away from the outer surface of the balloon at different angles, the elongated bodies each possessing a tip end and a side surface, at least some of the plurality of elongated bodies that are crystals of a water-insoluble drug possessing different lengths, the elongated bodies being positioned so that spaces exist between at least some of the elongated bodies that are adjacent one another; and
   a water-soluble additive layer provided on the outer surface of the balloon, the water-soluble additive layer filling the spaces that exist between at least some of the elongated bodies that are adjacent one another, the drug coating layer possessing an undulating outer surface, and the tip ends of at least some of the elongated bodies protruding outwardly beyond the additive layer so that the tip ends and side surfaces of the at least some of the elongated bodies are exposed outwardly of the additive layer.

2. The drug coating layer according to claim 1, wherein the additive layer comprises a first additive layer on the outer surface of the balloon, and a second additive layer covering an outside of the first additive layer and filling spaces between the elongated bodies protruding from the first additive layer.

3. The drug coating layer according to claim 2, wherein the first additive layer and the second additive layer comprise the same water-soluble compounds.

4. The drug coating layer according to claim 2, wherein the first additive layer and the second additive layer comprise different water-soluble compounds.

5. The drug coating layer according to claim 1, wherein the water-insoluble drug comprises at least one drug selected from the group consisting of rapamycin, paclitaxel, docetaxel, and everolimus.

6. The drug coating layer according to claim 1, wherein the elongated bodies have a length of 5 µm to 20 µm.

7. The drug coating layer according to claim 1, wherein all of the elongated bodies make up at least 50% of a total amount of drug crystals on the outer surface of the balloon, based on total volume of the crystals.

8. The drug coating layer according to claim 1, wherein a concentration of the water-soluble drug is between 0.1 µg/mm$^2$ and 10 µg/mm$^2$.

9. The drug coating layer according to claim 1, wherein the elongated bodies are independent of one another and not fixed to each other.

10. A balloon catheter comprising:

an elongated catheter main body possessing a distal portion and a proximal portion, a balloon fixed to the distal portion of the catheter main body and possessing an outer surface, a drug coating layer on the outer surface of the balloon, and a hub fixed to the proximal portion of the catheter main body;

the drug coating layer on the outer surface of the balloon comprising:

a plurality of upstanding elongated bodies that are crystals of a water-insoluble drug, the plurality of upstanding elongated bodies each possessing a proximal end and a longitudinal axis, the plurality of upstanding elongated bodies extending away from the outer surface of the balloon at different angles so that the longitudinal axes of the plurality of upstanding elongated bodies intersect the outer surface of the balloon, each of the upstanding elongated bodies possessing a tip end and a side surface, at least some of the upstanding elongated bodies possessing different lengths, the upstanding elongated bodies being positioned so that spaces exist between at least some of the elongated bodies that are adjacent one another, the proximal end of some of the upstanding elongated bodies being in contact with the outer surface of the balloon and the proximal end of others of the upstanding elongated bodies being spaced from the outer surface of the balloon so that a space exists between the proximal end of the other upstanding elongated bodies and the outer surface of the balloon;

a water-soluble additive layer on the outer surface of the balloon, the water-soluble additive layer being in contact with the outer surface of the balloon and extending from the outer surface of the balloon to adjacent the tip ends of the upstanding elongated bodies, the water-soluble additive layer filling the spaces between the upstanding elongated bodies that are adjacent one another, the water-soluble additive layer also filling the spaces between the outer surface of the balloon and the proximal end of the upstanding elongated bodies that are spaced from the outer surface of the balloon, the water-soluble additive layer being in contact with and connecting the tip ends of the upstanding elongated bodies to each other, the water-soluble additive layer also being in contact with and connecting the side surfaces of the upstanding elongated bodies to each other, the outer surface of the water-soluble additive layer being an undulating outer surface; and the tip end of a first plurality of the upstanding elongated bodies and a portion of the side surface adjacent the tip end of the first plurality of upstanding elongated bodies protruding outwardly beyond the outer surface of the additive layer so that the tip ends and side surfaces of the first plurality of upstanding elongated bodies are exposed outwardly of the additive layer.

11. The balloon catheter according to claim 10, wherein the water-soluble additive layer comprises a first additive layer on the outer surface of the balloon and a second additive layer covering an outside of the first additive layer and filling spaces between the upstanding elongated bodies protruding from the first additive layer.

12. The balloon catheter according to claim 10, wherein the first plurality of the upstanding elongated bodies protrude outwardly beyond the outer surface of the additive layer by no more than 1 µm.

13. The balloon catheter according to claim 12, wherein the upstanding elongated bodies have a length of 5 µm to 20 µm.

14. The balloon catheter according to claim 10, wherein the water-insoluble drug is at least one drug selected from the group consisting of rapamycin, paclitaxel, docetaxel, and everolimus.

15. A method for forming a drug coating layer on a balloon in which a plurality of elongated bodies are formed on a surface of the balloon, the elongated bodies being crystals of a water-insoluble drug and each crystal possessing a longitudinal axis, the method comprising:

applying a first coating solution comprising a water-insoluble drug, a first water-soluble additive, an organic solvent, and water to the surface of the balloon and evaporating the organic solvent and the water to form a first additive layer containing the first water-soluble additive and the elongated bodies protruding from the first additive layer such that at least one-half of a length of the elongated bodies protrudes from the first additive layer; and applying a second coating solution comprising a second water-soluble additive and water to the first additive layer and the elongated bodies and evaporating the water to form a second additive layer so as to fill a space between the elongated bodies protruding from the first additive layer.

16. The method for forming a drug coating layer according to claim 15, wherein the first water-soluble additive and the second water-soluble additive comprise the same water-soluble compounds.

17. The method for forming a drug coating layer according to claim 15, wherein the first water-soluble additive and the second water-soluble additive comprise different water-soluble compounds.

18. The method for forming a drug coating layer according to claim 15, wherein the water-insoluble drug comprises at least one drug selected from the group consisting of rapamycin, paclitaxel, docetaxel, and everolimus.

19. The method for forming a drug coating layer according to claim 15, wherein the elongated bodies have a length of 5 μm to 20 μm.

20. The method for forming a drug coating layer according to claim 15, wherein the method is performed such that all of the elongated bodies make up at least 50% of a total amount of drug crystals on the outer surface of the balloon, based on total volume of the crystals.

* * * * *